US011946927B2

(12) United States Patent
Yacyshyn et al.

(10) Patent No.: US 11,946,927 B2
(45) Date of Patent: *Apr. 2, 2024

(54) PROCESS AND SYSTEM FOR IDENTIFYING INDIVIDUALS HAVING A HIGH RISK OF INFLAMMATORY BOWEL DISEASE AND A METHOD OF TREATMENT

(71) Applicant: MUSIDORA BIOTECHNOLOGY LLC, Cincinnati, OH (US)

(72) Inventors: Bruce R. Yacyshyn, Cincinnati, OH (US); Mary E. Yacyshyn, Cincinnati, OH (US)

(*) Notice: Subject to any disclaimer, the term of this patent is extended or adjusted under 35 U.S.C. 154(b) by 937 days.

This patent is subject to a terminal disclaimer.

(21) Appl. No.: 16/545,349

(22) Filed: Aug. 20, 2019

(65) Prior Publication Data

US 2019/0376948 A1    Dec. 12, 2019

Related U.S. Application Data

(60) Continuation-in-part of application No. 16/369,242, filed on Mar. 29, 2019, now Pat. No. 11,199,534, which is a division of application No. 15/068,981, filed on Mar. 14, 2016, now Pat. No. 10,295,527.

(60) Provisional application No. 62/720,468, filed on Aug. 21, 2018.

(51) Int. Cl.
| | |
|---|---|
| G01N 33/49 | (2006.01) |
| A61K 31/196 | (2006.01) |
| A61K 31/606 | (2006.01) |

(52) U.S. Cl.
CPC ......... *G01N 33/492* (2013.01); *A61K 31/196* (2013.01); *A61K 31/606* (2013.01); *G01N 2800/065* (2013.01); *G01N 2800/067* (2013.01); *G01N 2800/50* (2013.01); *G01N 2800/52* (2013.01); *Y02A 50/30* (2018.01)

(58) Field of Classification Search
CPC ....... G01N 2800/065; G01N 2800/067; G01N 2800/50; G01N 2800/52; G01N 33/492
See application file for complete search history.

(56) References Cited

U.S. PATENT DOCUMENTS

| | | | |
|---|---|---|---|
| 7,923,544 B2 | 4/2011 | Garris | |
| 8,008,036 B2 | 8/2011 | Fallon | |
| 10,295,527 B2* | 5/2019 | Yacyshyn | ............ A61K 31/606 |
| 11,199,534 B2* | 12/2021 | Yacyshyn | ............ G01N 33/492 |
| 2005/0101568 A1 | 5/2005 | Kaila | |
| 2006/0063162 A1 | 3/2006 | Deng | |
| 2007/0020660 A1 | 1/2007 | Burczynski | |
| 2007/0087440 A1 | 4/2007 | Axford | |
| 2007/0155772 A1 | 7/2007 | Ise | |
| 2007/0178078 A1 | 8/2007 | Knoo | |
| 2008/0107650 A1 | 5/2008 | Tartaglia et al. | |
| 2008/0166719 A1* | 7/2008 | Lois | ............ G01N 33/74 |
| | | | 435/7.1 |
| 2008/0274118 A1 | 11/2008 | Aukerman | |
| 2009/0069564 A1 | 3/2009 | Kaila | |
| 2009/0117589 A1 | 5/2009 | Southern | |
| 2009/0196927 A1 | 6/2009 | Panitch | |
| 2009/0258848 A1 | 10/2009 | Chakravarti | |
| 2009/0299767 A1 | 12/2009 | Michon et al. | |
| 2009/0312376 A1 | 12/2009 | Rubio Royo | |
| 2010/0075891 A1 | 3/2010 | Ayalon-Soffer | |
| 2010/0093552 A1 | 4/2010 | Panja | |
| 2010/0130367 A1 | 5/2010 | Murthy | |
| 2010/0152062 A1 | 6/2010 | Harris | |
| 2010/0203522 A1 | 8/2010 | Lee | |
| 2010/0255508 A1 | 10/2010 | Gelzleichter | |
| 2010/0255513 A1 | 10/2010 | Denson | |
| 2010/0267037 A1 | 10/2010 | Westbrook | |
| 2010/0279275 A1 | 11/2010 | Panja | |
| 2011/0027771 A1 | 2/2011 | Deng | |
| 2011/0045476 A1 | 2/2011 | Barken | |
| 2011/0110924 A1 | 5/2011 | Lazar et al. | |
| 2011/0117111 A1 | 5/2011 | Kwon | |
| 2011/0003289 A1 | 6/2011 | Salk | |

(Continued)

FOREIGN PATENT DOCUMENTS

| | | |
|---|---|---|
| CN | 103149371 | 12/2015 |
| WO | WO2007047207 | 4/2007 |

(Continued)

OTHER PUBLICATIONS

International Search Report for Int App. No. PCT/US2019/047231, related to instant application and Written Opinion of Int. Searching Authority dated Nov. 19, 2019.
Supplementary European Search Report for related European Patent Application EP17767238.1 (PCT/US2017/022013) dated Nov. 11, 2019.
International Search report and Written Opinion, Int. App. No. PCT/US2017/022013, Filing Date Mar. 13, 2017.
Goral et al., "Antibodies to 70 kD and 90 kD heat shock proteins are associated with graft-versus-host dieses in peripheral blood stem cell transplant recipients," Clinical & Experimental Immunology, Mar. 31, 2002, vol. 127, No. 3, pp. 553-559.
Krouskou et al., "Apolipoprotein A-I inhibits experimental colitis and colitis-propelled carcinogenesis", Oncogene, Aug. 17, 2015, vol. 35, No. 19, pp. 2496-2505.

(Continued)

*Primary Examiner* — Brian Gangle
*Assistant Examiner* — Lakia J Jackson-Tongue
(74) *Attorney, Agent, or Firm* — Mark F. Smith; Smith Brandenburg Ltd

(57) ABSTRACT

A process and system directed to a more effective, individual based treatment regimen which is built on clinical identified predictive target biomarkers associated with predicting the risk of an individual developing IBD and includes one or more predictive panels of prediction target biomarkers that are used to determine the risk of an individual developing IBD for determining if a therapy should be administered to reduce the risk and further determines the efficacy of treating the individual with mesalamine and effectively identifies and validates novel drug targets for new IBD therapeutics, new diagnostics and diagnostics standards for IBD therapeutic strategies.

6 Claims, 26 Drawing Sheets

(56) References Cited

U.S. PATENT DOCUMENTS

| | | |
|---|---|---|
| 2011/0251101 A1 | 10/2011 | Li et al. |
| 2012/0171672 A1 | 7/2012 | Barken |
| 2013/0225439 A1 | 8/2013 | Princen et al. |
| 2013/0303391 A1 | 11/2013 | Li et al. |
| 2017/0261492 A1 | 9/2017 | Yacyshyn |

FOREIGN PATENT DOCUMENTS

| | | |
|---|---|---|
| WO | WO2007131575 A1 | 11/2007 |
| WO | WO2008043725 A1 | 4/2008 |
| WO | WO2008147562 A2 | 12/2008 |
| WO | WO2008153924 A2 | 12/2008 |
| WO | WO2009036099 A1 | 3/2009 |
| WO | WO2009046168 A1 | 4/2009 |
| WO | WO2009037572 A2 | 6/2009 |
| WO | WO2009120877 A2 | 10/2009 |
| WO | WO2010029578 | 3/2010 |
| WO | WO2010062663 | 3/2010 |
| WO | WO2010056337 | 5/2010 |
| WO | WO2010073266 | 7/2010 |
| WO | WO2010085658 | 7/2010 |
| WO | WO2010147714 A1 | 12/2010 |
| WO | WO2011033524 A2 | 3/2011 |
| WO | WO2011034597 A1 | 3/2011 |
| WO | WO2012037199 | 3/2012 |
| WO | WO2013059732 | 4/2013 |
| WO | WO2014104305 | 3/2014 |
| WO | WO2014182689 | 11/2014 |
| WO | WO2015067913 | 5/2015 |

OTHER PUBLICATIONS

Melgar et al., Local production of chemokines and prostaglandin E2 in the acute, chronic and recovery phase of murine experimental colitis, Cytokine, Nov. 7, 2006, vol. 35, Nos. 5-6, pp. 275-283.

Carter et al.. Functional correlates of the interleukin-1 receptor antagonist gene polymorphism in the colonic mucosa in ulcerative colitis,: Genes and Immunity, Jan. 31, 2014, vol. 5, No. 1, pp. 8-15.

Karagozian et al., "The role of mesalamine in the treatment of ulcerative colitis," Tharapeutics and Clinical Risk Mgt, 2007:3(5) 893-903.

AGA Abstracts, Su1187, 2015 SU1187, p. S-425.

Mortensen Joachim et al., Fragments of Citrullinated and MMP-Degraded Vimentin and MMP-Degraded Type II Collagen Are Novel Serological Biomarkers to Differentiate Crohn's Disease from Ulcerative Colitis, Journal of Crohn's and Colitis, vol. 9, No. 10, Jul. 18, 2015, pp. 863-872.

Extended European Search Report, dated Apr. 11, 2022 for corresponding European Patent Application No. 19852909.1.

Notificaation of Transmittal of International Preliminary Report on Patentability (including Report), corresponding PCT application No. PCT/US2019/047231 dated May 27, 2020.

\* cited by examiner

FIG. 3

Specific Biomarker Panels to be run based on gender and location

| Male & Female Pan/Extensive colitis FIRST PANEL - 112 | | | |
|---|---|---|---|
| Gene name | Analyte full name | Gene name | Analyte full name |
| GSTM1 | Glutathione S-Transferase mu 1 | RETN | Resistin |
| IL13 | Interleukin 13 | | AutoAb to Histone H4 |

| Female Left- Sided Colitis SECOND PANEL - 116 | | Male Left- Sided Colitis THIRD PANEL - 120 | |
|---|---|---|---|
| Gene name | Analyte full name | Gene name | Protein name |
| | Antibody to L. donovani | APOA1 | Apolipoprotein A-1 |
| | Antibody to HTLCV1/2 | PRL | Prolactin |
| | AutoAb to HSP90 alpha | IgA | Immunoglobuilin A |
| | | | AutoAb to HSP71 |

| Female Proctosigmoidtis FOURTH PANEL - 124 | | Male Proctosigmoiditis FIFTH PANEL - 128 | |
|---|---|---|---|
| Gene name | Analyte full name | Gene name | Protein name |
| CCL22 | MDC or Macrophage – derived chemokine | ILRN | IL 1 receptor antagonist |
| | Antibody to Cholera Toxin | CD40 L | CD40 ligand |

TABLE 1
MALE/FEMALE PAN/EXTENSIVE COLITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| GSTM1[1] | Glutathione S-Transferase mu 1 | 0.059 | -1.128 | -1.968 | Succeed |
| FABP | Fatty Acid Binding protein | 0.183 | -0.271 | -1.366 | Succeed |
| AFP | Alpha-fetoprotein | 0.186 | -0.328 | -1.355 | Succeed |
| IL7 | Interleukin 7 | 0.020 | 0.045 | 2.471 | Fail |
| SERPINA7 | Thyroxine binding globulin | 0.035 | 0.051 | 2.212 | Fail |
| RETN | Resistin | 0.047 | 0.446 | 2.080 | Fail |
| MPO | Myeloperoxidase | 0.049 | 0.002 | 2.061 | Fail |
| IL13 | Interleukin 13 | 0.054 | 0.049 | 2.017 | Fail |
| SERPINA1 | Alpha-1 antitrypsin | 0.055 | 1.231 | 2.004 | Fail |
| F7 | Coagulation Factor VII | 0.066 | 0.007 | 1.919 | Fail |
| ASP_C3a_des_arg | Cleavage product of complement component C3 activation | 0.072 | 0.001 | 1.870 | Fail |
| Testosterone | | 0.082 | 0.374 | 1.807 | Fail |
| B2M | Beta 2 microglobulin | 0.105 | 1.545 | 1.678 | Fail |
| S100A12 | S100 Calcium binding protein A12 (ENRAGE) | 0.110 | 0.018 | 1.654 | Fail |
| MMP3 | Matrix metallopeptidase 3 | 0.119 | 0.097 | 1.611 | Fail |
| IL3 | Interleukin 3 | 0.131 | 7.372 | 1.556 | Fail |
| C3 | Complement component C3 | 0.135 | 1.778 | 1.541 | Fail |
| APCS | Serum Amyloid P | 0.154 | 0.082 | 1.466 | Fail |
| Progesterone | | 0.157 | 0.194 | 1.454 | Fail |
| VCAM1 | Vascular cellular adhesion molecule 1 | 0.162 | 0.003 | 1.436 | Fail |
| SHBG | Sex hormone binding globulin | 0.163 | 0.026 | 1.434 | Fail |
| CXCL8 | Interleukin 8 | 0.182 | 0.029 | 1.368 | Fail |
| MUC16 | Mucin 16 ( CEA 125) | 0.191 | 0.073 | 1.340 | Fail |
| Antibody to infectious agent | | | | | |
| Hep B surface Ad | Ab to Hepatitis B surface antigen subtype Ad | 0.115 | -0.380 | -1.627 | Succeed |
| L.donovani | Ab to Leishmania donovani | 0.062 | 1.254 | 1.942 | Fail |
| Polio virus | Ab to Polio virus | 0.068 | 1.941 | 1.900 | Fail |
| CMV | Cytomegalovirus | 0.092 | 0.089 | 1.744 | Fail |
| Tetanus Toxoid | Ab to tetanus toxoid | 0.114 | 0.014 | 1.634 | Fail |
| Lyme | Ab to lyme disease | 0.131 | 0.049 | 1.558 | Fail |
| Rubeola | Ab to Rubeola | 0.162 | 0.435 | 1.436 | Fail |

[1] Bolded text represents statistically significant analytes associated with multivariate model and panel

FIG. 4B

TABLE 1(Continued)
MALE/FEMALE PAN/EXTENSIVE COLITIS
UNIVARIATE ANALYTES USED FOR MULTIVARIATE MODELING

| Gene | Full Name | P value | Estimate | T value | Succeed or Fail |
|---|---|---|---|---|---|
| *Autoantibody* | | | | | |
| COL2A1 | AutoAb to collagen type II | 0.181 | -0.596 | -1.373 | Succeed |
| H2A | AutoAb to Histone 2a | 0.042 | 0.781 | 2.135 | Fail |
| INS | AutoAb to Insulin | 0.070 | 1.310 | 1.887 | Fail |
| H4 | AutoAb to Histone 4 | 0.073 | 1.463 | 1.863 | Fail |
| GAD2 | AutoAb to Pancreatic islet cell glutamate decarboxylase | 0.160 | 1.232 | 1.444 | Fail |
| SSB | AutoAb to Sjogren Syndrome antigen B | 0.171 | 1.182 | 1.405 | Fail |

FIG. 5

TABLE 2

DESCRIPTIVE RANGES OF LOCATION AND GENDER SPECIFIC TARGET BIOMARKERS

| Location | Gender | Serological Markers | Unit | Mean | Std Error | Range | N total |
|---|---|---|---|---|---|---|---|
| Proctosigmoiditis | Male | IL1RN | pg/ml | 153.4208 | 11.4008 | 12.65-562 | 149 |
|  |  | CD40L | ng/ml | 1.6559 | 0.1097 | .0065-7.2 | 149 |
| Proctosigmoiditis | Female |  |  |  |  |  |  |
|  |  | CCL22 | pg/ml | 578.799 | 20.3739 | 58-1300 | 110 |
|  |  | Antibody to Cholera toxin | MFI ratio | 3.7836 | 0.0639 | 2.4-6.0 | 110 |
| Left-Sided | Male |  |  |  |  |  |  |
|  |  | HSP 71 autoantibody | MFI ratio | 3.0981 | 0.0855 | 1.6-7.1 | 106 |
|  |  | IgA | mg/ml | 3.6019 | 0.1748 | 0.55-9.4 | 106 |
|  |  | APOA1 | mg/ml | 0.3054 | 0.0128 | 0.13-0.91 | 106 |
|  |  | PRL | ng/ml | 2.3446 | 0.2313 | 0.18-16.9 | 106 |
| Left-Sided | Female |  |  |  |  |  |  |
|  |  | Antibody to L. donovani | MFI ratio | 3.233 | 0.0767 | 2.0-5.5 | 78 |
|  |  | Antibody to HTCLV 1/2 | MFI ratio | 4.6069 | 0.5432 | 2.2-36.42 | 78 |
|  |  | HSP90α autoantibody | MFI ratio | 8.4071 | 0.3094 | 2.8-15.25 | 78 |
| Extensive/Pancolitis MODEL 1 | Male/Female |  |  |  |  |  |  |
|  |  | GSTM1 | ng/ml | 1.2863 | 0.0705 | 0.15-1.7 | 76 |
|  |  | IL13 | pg/ml | 65.6357 | 3.0702 | 13.7-154.0 | 76 |
|  |  | Histone H2a autoantibody | MFI ratio | 4.4802 | 0.1263 | 2.7-8.0 | 76 |
| MODEL 2 |  | Histone H2a autoantibody | MFI ratio | 4.4802 | 0.1263 | 2.7-8.0 | 76 |
|  |  | RETN | ng/ml | 4.6947 | 0.2891 | 1.4-13.6 | 76 |

The mean values of protein levels listed were generated using the data produced using Rules-Based medicine MAP platform. Other protein measurement assays may obtain different values

FIG. 6

TABLE 3

PREDICTIVE MODELS FOR LOCATION AND GENDER

| Location | Gender | Effect Increment | Serological Markers | Estimate | Std. Error | p-value | Risk Ratio |
|---|---|---|---|---|---|---|---|
| Proctosigmoiditis AUC=.7188 | Male | 100pg/ml | IL1RN | .2844 | .0777 | .0004 | 1.3289 |
| | | 1ng/ml | CD40L | -.6412 | .1915 | .0010 | .5266 |
| | | NA | Intercept | -1.2293 | .2105 | <.0001 | NA |
| Proctosigmoiditis AUC=.7653 | Female | 100pg/ml | CCL22 | .2602 | .0640 | <.0001 | 1.2971 |
| | | .5 MFI ratio unit | Antibody to Cholera toxin | -.5882 | .2142 | .0071 | .5553 |
| | | NA | Intercept | .6750 | 1.4511 | .6428 | NA |
| Left-Sided AUC=.7462 | Male | 1 MFI ratio unit | HSP 71 autoantibody | .3800 | .1479 | .0116 | 1.4623 |
| | | 1 mg/ml | IgA | .1800 | .0789 | .0196 | 1.1973 |
| | | .1mg/ml | APOA1 | -.4925 | .2443 | .0465 | .6111 |
| | | 1 ng/ml | PRL | .1104 | .0509 | .0324 | 1.1167 |
| | | NA | Intercept | -2.3904 | .7046 | .001 | NA |
| Left-Sided AUC=.8546 | Female | 1 MFI ratio unit | Antibody to L. donovani | 1.2037 | .4226 | .0057 | 3.3325 |
| | | 1 MFI ratio unit | Antibody to HTCLV 1/2 | -.8790 | .3247 | .0084 | .4152 |
| | | 1 MFI ratio unit | HSP90α autoantibody | .2544 | .1096 | .0230 | 1.2897 |
| | | 4.8 vs 2.4 g/day | Dose | -1.1354 | .4337 | .0107 | .3213 |
| | | NA | Intercept | -4.385 | 1.9263 | .0270 | NA |
| Extensive/ Pancolitis | Male/ Female | | | | | | |
| MODEL 1 AUC=.8554 | | 1ng/ml | GSTM1 | -1.1553 | .4074 | .0059 | .3150 |
| | | 1pg/ml | IL13 | .1734 | .0741 | .0221 | 1.1893 |
| | | 1 MFI ratio unit | Histone H2a autoantibody | .4988 | .2539 | .0533 | 1.6467 |
| | | NA | Intercept | -3.7842 | 1.4528 | .0112 | NA |
| MODEL 2 AUC=.7883 | | 1 MFI ratio unit | Histone H2a autoantibody | .4001 | .1222 | .0016 | 1.4920 |
| | | 1ng/ml | RETN | .1296 | .0550 | .0212 | 1.1384 |
| | | | Intercept | -4.0207 | .8759 | <.0001 | NA |

FIG. 7

TABLE 4
FEMALE LEFT – SIDED COLITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| Progesterone | | 0.068 | -0.156 | -1.847 | Succeed |
| ACE | Angiotensin 1 converting enzyme | 0.161 | -0.01 | -1.416 | Succeed |
| CKMB | Creatine kinase (M muscle) or (B brain) | 0.092 | 3.418 | 1.709 | Fail |
| CCL4 | Mip1 beta | 0.092 | 0.003 | 1.707 | Fail |
| CALCA | Calcitonin | 0.116 | 0.162 | 1.589 | Fail |
| CCL5 | RANTES | 0.148 | 0.021 | 1.463 | Fail |
| VEGF | Vascular endothelial growth factor | 0.185 | 0.0005 | 1.338 | Fail |
| IL7 | Interleukin 7 | 0.189 | 0.008 | 1.326 | Fail |
| Antibody to infectious agent | | | | | |
| T. pallidum 15Kd | Ab to Treponema pallidum recombinant 15Kd protein | 0.078 | -0.096 | -1.788 | Succeed |
| HTLCV1/2 | Ab to Human T cell lymphotrophic virus 1/2 | 0.088 | -0.799 | -1.728 | Succeed |
| HSV 1/2 | Herpes Simplex virus 1/2 | 0.134 | -0.043 | -1.515 | Succeed |
| Hep C NS3 | Ab to Hepatitis C non-structural protein 3 | 0.136 | -0.808 | -1.505 | Succeed |
| Cholera Toxin | Ab to Cholera Toxin | 0.147 | -0.729 | -1.464 | Succeed |
| Hep E orf2 6KD | Ab to Hepatitis E open reading frame 2 (major capsid protein) 6Kd | 0.179 | -0.877 | -1.356 | Succeed |
| L.donovani | Ab to Leishmania donovani | 0.087 | 0.669 | 1.732 | Fail |
| ASCA | Ab to Saccharomyces cervisiae (antibody to cell wall) | 0.174 | 0.294 | 1.371 | Fail |
| Autoantibody | | | | | |
| HSC 70 (HSPA8) | AutoAb to Heat Shock cognate protein 70 (constitutively expressed) | 0.151 | -0.737 | -1.451 | Succeed |
| Centromere B (CENPB) | AutoAb to centromere protein B | 0.075 | 0.214 | 1.806 | Fail |
| HSP90 alpha (HSP90AA1) | AutoAb to heat shock protein 90KD alpha | 0.091 | 0.173 | 1.712 | Fail |
| SCl 70 | AutoAb to topisomerase type 1 | 0.103 | 0.273 | 1.648 | Fail |
| Mitochondria | AutoAb to mitochondrial proteins | 0.13 | 0.107 | 1.529 | Fail |
| HSP71 (HSPA8) | AutoAb to Heat shock protein 70 (inducible) | 0.188 | 0.324 | 1.328 | Fail |

Bolded text represents statistically significant analytes associated with multivariate model and panel

FIG. 8A
TABLE 5
MALE LEFT –SIDED COLITIS
UNIVARIATE ANALYTES USED FOR MULTIVARIATE MODELING

Bolded text represents statistically significant analytes associated with multivariate model and panel

| Gene | Full Name | P value | Estimate | T value | Succeed or Fail |
|---|---|---|---|---|---|
| Protein | | | | | |
| IL7 | Interleukin 7 | 0.033 | -0.018 | -2.15 | Succeed |
| IL13 | Interleukin 13 | 0.102 | -0.016 | -1.65 | Succeed |
| CEA | Carcinoembryonic Antigen | 0.114 | -0.398 | -1.59 | Succeed |
| APOA1 | Apolipoprotein A-1 | 0.13 | -3.668 | -1.52 | Succeed |
| ACE | Angiotensin 1 converting enzyme | 0.131 | -0.009 | -1.52 | Succeed |
| THPO | Thrombopoietin | 0.137 | -0.385 | -1.5 | Succeed |
| CKM | Creatine Kinase Brain/Muscle | 0.146 | -2.407 | -1.46 | Succeed |
| LPA | Lipoprotein A | 0.17 | -0.004 | -1.37 | Succeed |
| CCL2 | Monocyte chemotactic protein 1 | 0.182 | -0.002 | -1.34 | Succeed |
| A2M | Alpha 2 macroglobulin | 0.197 | -1.19 | -1.29 | Succeed |
| MMP9 | Matrix metallopeptidase -9 | 0.075 | 0.062 | 1.8 | Fail |
| LEP | Leptin | 0.097 | 0.074 | 1.67 | Fail |
| PRL | Prolactin | 0.099 | 0.150 | 1.66 | Fail |
| GSTM1 | Glutathione S-Transferase mu 1 | 0.109 | 0.688 | 1.62 | Fail |
| IgA | Immunoglobulin A | 0.146 | 0.189 | 1.47 | Fail |
| CRP | C - reactive protein | 0.158 | 0.051 | 1.42 | Fail |
| Progesterone | | 0.161 | 0.081 | 1.41 | Fail |
| CALCA | Calcitonin | 0.182 | 0.062 | 1.34 | Fail |
| Antibody to infectious agent | | | | | |
| V Zoster | Ab to Varicella Zoster | 0.029 | 0.049 | 2.21 | Fail |
| HSV 1gD | Ab to Herpes Simplex virus type 1 glycoprotein D | 0.061 | 0.006 | 1.9 | Fail |
| HSV2gG | Ab to Herpes Simplex virus type 1 glycoprotein G | 0.069 | 0.008 | 1.84 | Fail |
| M.Tuberculosis | Ab to Mycobacterium Tuberculosis | 0.072 | 0.084 | 1.82 | Fail |
| EBNA | Ab to epstein barr virus nuclear antigen | 0.08 | 0.007 | 1.77 | Fail |
| T pallidum 15Kd | Ab to Treponema pallidum recombinant 15Kd protein | 0.095 | 0.051 | 1.68 | Fail |
| HSV ½ | Ab to Herpes Simplex virus 1/2 | 0.152 | 0.028 | 1.44 | Fail |
| Hep A | Ab to Hepatitis A | 0.154 | 0.136 | 1.44 | Fail |

FIG. 8B

TABLE 5 (continuation)
MALE LEFT –SIDED COLITIS
UNIVARIATE ANALYTES USED FOR MULTIVARIATE MODELING

| | Autoantibody | | | | |
|---|---|---|---|---|---|
| pANCA | AutoAb to myeloperoxidase | 0.012 | 0.416 | 2.56 | Fail |
| Collagen type 1 | AutoAb to collagen type 1 | 0.027 | 0.006 | 2.24 | Fail |
| Mitochondria | AutoAb to mitochondrial proteins | 0.085 | 0.235 | 1.74 | Fail |

FIG. 9

TABLE 6
FEMALE PROCTOSIGMOIDITIS
UNIVARIATE ANALYTES USED FOR MULTIVARIATE MODELING

| Gene | Full Name | P value | Estimate | T value | Succeed or Fail |
|---|---|---|---|---|---|
| *Protein* | | | | | |
| FABP (2or 4) | Fatty acid binding protein 2 or 4 | 0.099 | -0.223 | -1.665 | Succeed |
| C3a | ASPC3a des arg | 0.113 | -0.001 | -1.596 | Succeed |
| Testosterone | | 0.115 | -1.037 | -1.587 | Succeed |
| CD40LG | CD40 ligand | 0.164 | -0.341 | -1.401 | Succeed |
| IFNG | Interferon gamma | 0.182 | -0.289 | -1.341 | Succeed |
| CCL22 | Monocyte derive cytokine | 0.010 | 0.003 | 2.622 | Fail |
| CGA/TSHb | thyroid stimulating hormone alpha/beta | 0.046 | 0.480 | 2.022 | Fail |
| FGF2 | Fibroblast growth factor 2 | 0.072 | 0.006 | 1.817 | Fail |
| IL2 | Interleukin 2 | 0.127 | 0.148 | 1.537 | Fail |
| IL25 | Interleukin 25 | 0.132 | 0.038 | 1.517 | Fail |
| VWF | Von Willebrands factor | 0.179 | 0.019 | 1.352 | Fail |
| *Antibody to infectious agent* | | | | | |
| Cholera Toxin | Ab to Cholera Toxin | 0.020 | -1.145 | -2.352 | Succeed |
| L.donovani | Ab to Leishmania donovani | 0.024 | -1.228 | -2.282 | Succeed |
| Strept O SLO | Ab to Streptococcal Streptolysin oxygen labile exotoxin | 0.054 | -0.055 | -1.942 | Succeed |
| CMV | Ab to Cytomegalovirus | 0.065 | -0.092 | -1.863 | Succeed |
| Hep B core | Ab to Hepatitis B core protein | 0.086 | -0.381 | -1.731 | Succeed |
| H. pylori | Ab to H. pylori | 0.109 | -0.022 | -1.617 | Succeed |
| Hep A | Ab to Hepatitis A | 0.135 | -0.255 | -1.505 | Succeed |
| Hep B Env | Ab to Hepatitis B envelope protein | 0.144 | -0.212 | -1.472 | Succeed |
| Tetanus Toxoid | Ab to tetanus toxoid | 0.023 | 0.009 | 2.297 | Fail |
| EBNA | Ab to epstein barr virus nuclear antigen | 0.091 | 0.011 | 1.178 | Fail |
| Lyme | Ab to lyme disease | 0.094 | -0.049 | -1.688 | Fail |
| Influenza A H3N2 | Ab to Influenza A H3N2 | 0.101 | 0.003 | 1.562 | Fail |
| Hep C NS3 | Ab to Hepatitis C non-structural protein 3 | 0.120 | 0.302 | 1.568 | Fail |
| HTLCV1/2 | Ab to Human T cell lymphotrophic virus 1/2 | 0.175 | 0.037 | 1.364 | Fail |
| *Autoantibody* | | | | | |
| Histone H4 | AutoAb to Histone H4 | 0.102 | -0.687 | -1.646 | Succeed |
| GAD | AutoAb to Pancreatic islet cell glutamate decarboxylase | 0.174 | -0.801 | -1.368 | Succeed |
| Mitochondria | AutoAb to mitochondrial proteins | 0.128 | 0.000 | 1.531 | Fail |
| Thyroglobuilin | AutoAb to Thyroglobulin | 0.175 | 0.029 | 1.366 | Fail |
| T3 | AutoAb to triiodothyronine | 0.179 | 0.207 | 1.351 | Fail |

FIG. 10

TABLE 7
MALE PROCTOSIGMOIDITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| CD40LG | CD40 ligand | 0.007 | -0.559 | -2.739 | Succeed |
| EGF | Epidermal growth factor | 0.009 | -0.005 | -2.655 | Succeed |
| THPO | Thrombopoietin | 0.043 | -0.455 | -2.037 | Succeed |
| IgE | Immunoglobulin E | 0.131 | -0.016 | -1.517 | Succeed |
| KLK3 | Prostate Specific Antigen (PSA), Free | 0.172 | -1.750 | -1.369 | Succeed |
| IL25 | Interleukin 25 | 0.199 | -0.102 | -1.291 | Succeed |
| A2M | Alpha 2 macroglobulin | 0.047 | 1.515 | 2.000 | Fail |
| ILRN | Interleukin 1 Receptor Antagonist | 0.062 | 0.002 | 1.878 | Fail |
| CALCA | Calcitonin | 0.153 | 0.077 | 1.435 | Fail |
| IL2 | Interleukin 2 | 0.155 | 0.164 | 1.426 | Fail |
| CXCL8 | Interleukin 8 | 0.158 | 0.007 | 1.417 | Fail |
| GCG | Glucagon | 0.177 | 0.030 | 1.357 | Fail |
| PRL | Prolactin | 0.188 | 0.048 | 1.322 | Fail |
| CGA/THS | Thyroid stimulating hormone | 0.584 | 0.228 | 1.907 | Fail |
| Antibody to Infectious Agent | | | | | |
| Hep A | Ab to Hepatitis A | 0.071 | -0.220 | -1.814 | Succeed |
| M Tuberculosis | Ab to Mycobacterium Tuberculosis | 0.141 | -0.087 | -1.479 | Succeed |
| H. Pylori | Ab to H. pylori | 0.198 | -0.006 | -1.292 | Succeed |
| L donovani | Ab to Leishmania donovani | 0.049 | 0.578 | 1.981 | Fail |
| T. Cruzi | Ab to Trypanosoma Cruzi | 0.064 | 0.324 | 1.869 | Fail |
| Hep C NS5 | Ab to Hepatitis C non-structural protein 5 | 0.126 | 0.462 | 1.539 | Fail |
| HIV1 p24 | Ab to HIV 1 p24 (gag or capsid p24) | 0.171 | 0.294 | 1.374 | Fail |
| Autoantibody | | | | | |
| HSC70 | AutoAb to Heat Shock cognate protein 70 (constitutively expressed) | 0.064 | -0.694 | -1.869 | Succeed |
| C1q | AutoAb to complement protein C1q | 0.098 | -0.019 | -1.663 | Succeed |
| cANCA | AutoAb to proteinase 3 | 0.052 | 0.062 | 1.955 | Fail |
| Insulin | AutoAb to Insulin | 0.067 | 0.424 | 1.844 | Fail |
| Thyroglobulin | AutoAb to Thyroglobulin | 0.069 | 0.036 | 1.834 | Fail |
| T3 | AutoAb to triiodothyronine | 0.136 | 0.185 | 1.498 | Fail |

Bolded text represents statistically significant analytes associated with multivariate model and panel

FIG. 11

Table 8
MALE

| Gene | Protein | Indication of Location (bolded - odds ratio greater than 1.3 or less than .775) |
|---|---|---|
| SERPINA1 | Alpha-1 antitrypsin | Proct M < LS M < Ext/Pan M |
| CD40L | CD40 ligand | Proct M < LS M < Ext/Pan M |
| FGF2 | Fibroblast growth factor 2 | Proct M < LS M < Ext/Pan M |
| CCL22 | Macrophage derived chemokine | Proct M ≤ LS M < Ext/Pan M |
| RETN | Resistin | Proct M < LS M < Ext/Pan M |
| TNFRSF1B | Tumor necrosis factor receptor superfamily member 1B | Proct M < LS M < Ext/Pan M |
| CALCA | Calcitonin | Proct M < LS M < Ext/Pan M |
| MUC16 Or CA19.9 | Ca 125 Ca19.9 | Proct M < LS M < Ext/Pan M |
| ICAM1 | ICAM-1 | Proct M < LS M < Ext/Pan M |
| SERPINE1 | Plasminogen Activator Inhibitor 1 | Proct M < LS M < Ext/Pan M |
| cANCA | AutoAb to proteinase 3 (cytoplasmic) | Proct M < LS M < Ext/Pan M |
| CCL11 | Eotaxin-1 | Proct M < Ext/Pan M < LS M |
|  | Antibodies to T. Cruzi | LS M < Proct M < Ext/Pan M |

Bolded text represents statistically significant analytes associated with multivariate model and panel

FIG. 12

TABLE 9
MALE LOCATIONS

Proctosigmoiditis Male

| Gene | Protein | Indication of Location | | |
|---|---|---|---|---|
| SERPINA1 | Alpha-1 antitrypsin | Proct M<LS M | p= .036 | OR 1.6 |
| | | Proct M <Ext/Pan M | p= .004 | OR 2.19 |
| CALCA | Calcitonin | Proct M<LS M | p= .040 | OR 1.064 |
| | | Proct M <Ext/Pan M | p= .036 | OR 1.082 |
| MUC16 Or CA19.9 | Ca 125 Ca19.9 | Proct M<LS M | p= .0006 | OR 1.034 |
| | | Proct M <Ext/Pan M | p= .0004 | OR 1.037 |
| CCL11 | Eotaxin-1 | Proct M<LS M | p= .0003 | OR 1.003 |
| | | Proct M <Ext/Pan M | p= .034 | OR 1.002 |
| ICAM1 | ICAM-1 | Proct M<LS M | p= .016 | OR 1.008 |
| | | Proct M <Ext/Pan M | p= .0069 | OR 1.011 |
| SERPINE1 | Plasminogen Activator Inhibitor 1 | Proct M<LS M | p= .039 | OR 1.002 |
| | | Proct M <Ext/Pan M | p= .005 | OR 1.005 |
| | cANCA Autoantibodies to proteinase 3 (cytoplasmic) | Proct M<LS M | p= .040 | OR 1.042 |
| | | Proct M <Ext/Pan M | p= .037 | OR 1.046 |

Left-Sided Male

| Gene | Protein | Indication of Location | | |
|---|---|---|---|---|
| TNFRSF1B | Tumor necrosis factor receptor superfamily member 1B | LS M>Proct M | p=. 014 | OR .814 |
| | | LS M<Ext/Pan M | p= .021 | OR 1.247 |

Extensive/Pancolits Male

| Gene | Protein | Indication of Location | | |
|---|---|---|---|---|
| CD40L | CD40 ligand | Ext/Pan M >LS M | p= .023 | OR .774 |
| | | Ext/Pan M > Proct M | p= .012 | OR .765 |
| FGF2 | Fibroblast growth factor 2 | Ext/Pan M >LS M | p= .044 | OR .995 |
| | | Ext/Pan M >Proct M | p= .0009 | OR .993 |
| CCL22 | Macrophage derived chemokine | Ext/Pan M >LS M | p= .025 | OR .998 |
| | | Ext/Pan M > Proct M | p= .022 | OR .998 |
| RETN | Resistin | Ext/Pan M >LS M | p= .0009 | OR .819 |
| | | Ext/Pan M > Proct M | p= .00001 | OR .728 |
| | Antibodies to T. Cruzi | Ext/Pan M >LS F | p= .019 | OR .722 |
| | | Ext/Pan M > Proct M | p= .022 | OR .743 |
| TNFRSF1B | Tumor necrosis factor receptor superfamily member 1B | Ext/Pan M >LS F | p= .021 | OR .801 |
| | | Ext/Pan M > Proct F | p= .00003 | OR .652 |

FIG. 13

TABLE 10 MALE

| GENE or Antibody | PROTOSIGMOIDITIS | | | LEFT-SIDED | | | PAN/EXTENSIVE | | |
|---|---|---|---|---|---|---|---|---|---|
| | average | median | range | average | median | range | average | median | range |
| SERPINA1 (mg/ml) | 1.75 | 1.70 | .90-4 | 1.90 | 1.80 | .99-3.7 | 2.03 | 1.85 | 1-4.2 |
| MUC 16 (U/ml) | 11.91 | 10.50 | 4.35-50.10 | 15.13 | 14.80 | 4.35-36.4 | 19.79 | 11.35 | 4.35-316 |
| CA19.9 (U/ml) | 7.14 | 5.00 | .78-38.60 | 10.95 | 6.15 | .78-106 | 8.98 | 5.35 | .8-56.4 |
| CALCA (pg/ml) | 8.11 | 6.50 | 1.60-20.50 | 9.24 | 8.30 | 1.6-32.9 | 9.62 | 8.30 | 1.6-24.5 |
| CD40L (ng/ml) | 1.66 | 1.40 | .01-7.2 | 1.68 | 1.35 | .04-9 | 2.31 | 2.10 | .0065-7 |
| CCL11 (pg/ml) | 238.61 | 210.00 | 9.50-736 | 333.51 | 268.50 | 55.10-1840 | 291.39 | 268.00 | 9.5-1100 |
| CCL22 (pg/ml) | 560.84 | 532.00 | 185-1580 | 556.95 | 538.50 | 236-1160 | 656.37 | 612.50 | 49.9-2080 |
| SERPINE1 (ng/ml) | 240.06 | 234.00 | 36.9-458 | 265.53 | 256.00 | 64.60-621 | 287.61 | 276.00 | 117-821 |
| RETN (ng/ml) | 3.52 | 3.20 | .93-12.70 | 3.90 | 3.55 | .96-11.80 | 4.99 | 4.15 | 1.4-13.6 |
| TNFRSF1B (ng/ml) | 4.32 | 4.20 | 1.60-9.10 | 4.82 | 4.60 | 2-10.10 | 5.60 | 4.95 | 2.5-12.6 |
| Antibodies to T. Cruzi (MFI) | 4.15 | 4.00 | 2-10.4 | 4.12 | 3.80 | 1.6-9.7 | 4.65 | 4.40 | 2.1-8.5 |
| cANCA (MFI) | 6.00 | 4.60 | 1.60-42.25 | 8.44 | 5.00 | 2-100.33 | 9.07 | 5.30 | 2.6-42.7 |
| FGF2 | 121.20 | 107.00 | 52-329 | 135.15 | 105.00 | 52-329 | 339.50 | 322.2 | 248-578 |

FIG. 14

<u>Table 11</u>
FEMALE

| Gene/Antigen | Protein | Indication of Location (bolded - odds ratio greater than 1.3) |
|---|---|---|
| SERPINA1 | Alpha-1 antitrypsin | Proct F < LS F < Ext/Pan F |
| B2M | Beta 2 microglobulin | Proct F < LS F < Ext/Pan F |
| C3 | ASP (C3a des Arg) | Proct F < LS F ≤ Ext/Pan F |
| MMP3 | Matrix metallopeptidase 3 | Proct F < LS F < Ext/Pan F |
| RETN | Resistin | Proct F < LS F < Ext/Pan F |
| IL6 | Interleukin 6 | Proct F < LS F < Ext/Pan F |
| TNFRSF1B | Tumor necrosis factor receptor superfamily member 1B | Proct F < LS F < Ext/Pan F |
|  | Antibodies to CMV | Proct F < LS F < Ext/Pan F |
|  | Antibodies to Lyme | Proct F < LS F < Ext/Pan F |
| F7 | Coagulation Factor VII | Proct F ≤ Ext/Pan F < LS F |
| SERPINA7 | Thyroxin binding globulin | Proct F < Ext/Pan F < LS F |
| IFNG | Gamma Interferon | LS F < Proct F < Ext/Pan F |
|  | Auto antibody to RNPa | LS F < Proct F < Ext/Pan F |
|  | Auto antibody to RNP | LS F < Proct F < Ext/Pan F |
| GSTM1 | Glutathione S-Transferase Mu-1 | LS F < Ext/Pan F < Proct F |
| BDNF | Brain derived neurotrophic factor | Ext/Pan F < LS F < Proct F |
| THPO | Thrombopoietin | Ext/Pan F < LS F ≤ Proct F |

FIG. 15

TABLE 12
FEMALE LOCATIONS

Proctosigmoiditis Female

| Gene | Protein | Indication of Location | | |
|---|---|---|---|---|
| SERPINA1 | Alpha-1 antitrypsin | Proct F<LS F | p= .002 | OR 2.3 |
| | | Proct F <Ext/Pan F | p= .0004 | OR 3.31 |
| C3 | ASP (C3a des Arg) | Proct F<LS F | p= .037 | OR 1.0005 |
| | | Proct F <Ext/Pan F | p= .041 | OR 1.0007 |
| B2M | Beta 2 microglobulin | Proct F<LS F | p= .021 | OR 2.058 |
| | | Proct F <Ext/Pan F | p= .008 | OR 2.826 |
| F7 | Coagulation Factor VII | Proct F<LS F | p= .0008 | OR 1.003 |
| | | Proct F <Ext/Pan F | p= .048 | OR 1.002 |
| MMP3 | Matrix metallopeptidase 3 | Proct F<LS F | p= .028 | OR 1.092 |
| | | Proct F <Ext/Pan F | p= .016 | OR 1.124 |
| RETN | Resistin | Proct F<LS F | p= .004 | OR 1.386 |
| | | Proct F <Ext/Pan F | p= .002 | OR 1.546 |
| SERPINA7 | Thyroxin binding globulin | Proct F<LS F | p= .002 | OR 1.024 |
| | | Proct F <Ext/Pan F | p= .018 | OR 1.024 |
| TNFRSF1B | Tumor necrosis factor receptor superfamily member 1B | Proct F<LS F | p= .023 | OR 1.243 |
| | | Proct F<Ext/Pan F | p= .022 | OR 1.326 |

Left Sided Female

| Gene | Protein | Indication of Location | | |
|---|---|---|---|---|
| GSTM1 | Glutathione S-Transferase Mu-1 | LS F< Proct F | p=. 031 | OR 1.656 |
| | | LS F< Ext/Pan F | p= .073 | OR 1.91 |
| IFNG | Gamma Interferon | LS F< Proct F | p= 109 | OR 1.18 |
| | | LS F< Ext/Pan F | p= .016 | OR 1.34 |

Extensive/Pancolits Female

| Gene | Protein | Indication of Location | | |
|---|---|---|---|---|
| BDNF | Brain derived neurotrophic factor | Ext/Pan F <LS F | p= .004 | OR 1.08 |
| | | Ext/Pan F < Proct F | p= .008 | OR 1.07 |
| THPO | Thrombopoietin | Ext/Pan F <LS F | p= .005 | OR 1.88 |
| | | Ext/Pan F < Proct F | p= .004 | OR 1.87 |
| | | | | |
| | Antibodies to CMV | Ext/Pan F >LS F | p= .057 | OR .942 |
| | | Ext/Pan F > Proct F | p= .036 | OR .940 |
| | Antibodies to Lyme | Ext/Pan F >LS F | p= .058 | OR .964 |
| | | Ext/Pan F > Proct F | p= .027 | OR .960 |
| | Auto antibody to RNPa | Ext/Pan F >LS F | p= .039 | OR .922 |
| | | Ext/Pan F > Proct F | p= .091 | OR .964 |
| | Auto antibody to RNP | Ext/Pan F >LS F | p= .037 | OR .922 |
| | | Ext/Pan F > Proct F | p= .089 | OR .976 |
| IL6 | Il 6 | Ext/Pan F >LS F | p= .074 | OR .930 |
| | | Ext/Pan F > Proct F | p= .047 | OR .927 |

FIG. 16

FEMALE- TABLE 13

| GENE or Antibody | PROTOSIGMOIDITIS | | | LEFT-SIDED | | | PAN/EXTENSIVE | | |
|---|---|---|---|---|---|---|---|---|---|
| | mean | median | range | mean | median | range | mean | median | range |
| SERPINA1 (mg/ml) | 1.65 | 1.60 | 0.92-3.10 | 1.92 | 1.75 | 0.75 - 4.40 | 2.11 | 1.95 | 0.78 - 3.80 |
| C3 (ASP C3a des Arg) (ng/ml) | 2733 | 2685 | 1710- 4380 | 2913 | 2795 | 1980-6530 | 2968 | 2915 | 1890 - 4350 |
| B2M (µg/ml) | 1.38 | 1.30 | 0.5-4.00 | 1.55 | 1.50 | 0.67 - 2.90 | 1.66 | 1.60 | 0.54 - 2.80 |
| BDNF (ng/ml) | 19.09 | 18.15 | 2.4 - 41.00 | 19.73 | 19.00 | 0.96 - 44.90 | 14.26 | 13.40 | 1.3 - 33.60 |
| F7 (ng/ml) | 429.53 | 411 | 110-861 | 518.09 | 495.50 | 135 - 1490 | 490.57 | 496 | 199 - 685 |
| IL6 (pg/ml) | 2.78 | 0.92 | 0.82-30.80 | 2.81 | 1.85 | 0.82 - 22.70 | 4.84 | 1.70 | 0.78 - 22.80 |
| MMP3 (ng/ml) | 5.45 | 4.70 | 0.033-17.40 | 6.76 | 5.70 | 0.033 - 20.50 | 7.50 | 6.20 | 1.3 - 29.70 |
| RETN (ng/ml) | 3.32 | 3.15 | 1.5 - 10.60 | 3.93 | 3.90 | 2 - 9.30 | 4.24 | 3.85 | 1.4 - 9.00 |
| SERPINA7 (µg/ml) | 56.78 | 54.10 | 23 -110 | 65.52 | 62.45 | 31.9 - 124 | 66.24 | 63.45 | 23.6 - 128 |
| TNFRSF1B (ng/ml) | 4.05 | 3.75 | 1.7 - 10.80 | 4.57 | 4.40 | 1.7 - 10.10 | 4.81 | 4.65 | 1.5 - 10.30 |
| THPO (ng/ml) | 3.53 | 3.40 | 0.85 - 8.20 | 3.54 | 3.40 | 1.7 - 7.00 | 2.86 | 3.05 | 0.58 - 4.10 |
| Antibodies to CMV (MFI) | 14.02 | 13.90 | 2.8 -31.00 | 14.35 | 13.98 | 3.5 - 32.25 | 16.99 | 15.05 | 4.2 - 37.25 |
| Antibodies to Lyme (MFI) | 20.28 | 20.37 | 2.1 - 47.38 | 21.20 | 19.90 | 2.7 - 47.50 | 25.54 | 22.83 | 5.7 - 52.88 |
| Auto antibody to RNPa (MFI) | 5.77 | 4.25 | 2 - 44.83 | 4.79 | 3.55 | 1 - 29.00 | 9.23 | 4.95 | 2 - 74.80 |
| Auto antibody to RNP (MFI) | 33.79 | 33.54 | 3-77.88 | 32.19 | 30.81 | 2.7-86 | 39.08 | 39.15 | 14.35-73.25 |
| IFNG | 2.42 | 2.01 | ND[a]-8.16 | 2.36 | 2.09 | ND[a]-9.06 | 2.70 | 1.72 | ND[a]-12.90 |
| GSTM1 | 0.40 | 0.38 | ND[a]-0.77 | 0.36 | 0.31 | ND[a]-0.85 | 0.46 | 0.40 | ND[a]-.89 |

ND[a] = not detectable

FIG. 17

```
IDENTIFYING GENDER OF A PATIENT DIAGNOSED WITH UC
STEP 300
          │
DETERMINING THE LOCATION OF THE UC
STEP 302
          │
TAKE A FIRST VENOUS BLOOD SAMPLE FROM PATIENT
STEP 304
          │
MIX BLOOD SAMPLE WITH ONE OR MORE SEPARATORS TO
CREATE A FIRST BLOOD COMPONENT
STEP 306
          │
SELECT APPROPRIATE PANEL AND IDENTIFY THE
PRESENCE OF ONE OR MORE TARGET BIOMARKERS IN THE
FIRST BLOOD COMPONENT
STEP 308
          │
DETERMINE LEVELS OF TARGET BIOMARKERS IN FIRST
BLOOD COMPONENT
STEP 310
          │
GIVE MEDICATION TO PATIENT
STEP 312
          │
TAKE A SECOND VENOUS BLOOD SAMPLE FROM PATIENT
STEP 314
          │
MIX SECOND BLOOD SAMPLE WITH ONE OR MORE
SEPARATORS TO CREATE A SECOND BLOOD COMPONENT
STEP 316
          │
COMPARE LEVELS OF TARGET BIOMARKERS OF THE FIRST
BLOOD COMPONENT WITH LEVELS IN THE SECOND BLOOD
COMPONENT TO CREATE AN OUTCOME THAT PREDICTS
THE EFFICACY OF THE ADMINISTERED MEDICATION
STEP 318
```

PROCESS AND SYSTEM FOR IDENTIFYING INDIVIDUALS HAVING A HIGH RISK OF INFLAMMATORY BOWEL DISEASE AND A METHOD OF TREATMENT

This application is a continuation-in part of U.S. patent application Ser. No. 16/369,242, filed Mar. 29, 2019 and claims benefit to and incorporates in its entirety U.S. Provisional Patent Application No. 62/720,468 filed Aug. 21, 2018. Further, U.S. patent application Ser. No. 16/369,242 is a divisional patent application of U.S. patent application Ser. No. 15/068,981, filed Mar. 14, 2016.

This invention was made in the performance of a Cooperative Research and Development Agreement with the Department of the Army. The invention may be manufactured and used by the Government of the United States for all government purposes without the payment of any royalty.

BACKGROUND OF THE INVENTION

Inflammatory bowel diseases (IBD), Crohn's and ulcerative colitis (UC) are chronic multifactorial diseases that involve both genetics and environment of the effected patient. These diseases are progressive, remitting and relapsing throughout a patient's lifetime. Over the past 15 years genome wide association studies (GWAS) have been carried out on IBD patients' and their families resulting in over 200 genes with greater than 1 million single nucleotide polymorphisms (SNPs) potentially contributing to IBD etiology. It is very rare to have monogenetic causes of IBD. Most cases are polygenic with environmental contribution.

Ulcerative colitis (UC) is a form of inflammatory bowel disease (IBD) that appears in the large intestine or colon with periods of exacerbated symptoms and periods that are relatively symptom free. UC patients often experience the same symptoms as irritable bowel syndrome (IBS) patients, which is a much less serious condition, making a definitive diagnosis much more complicated. Similarly, patients with indeterminate colitis may have a form of colitis that is different from UC, and more similar to Crohn's colitis, another related form of intestinal IBD.

Symptoms of UC are anatomically heterogeneous in their presentation between patients. UC patients for example can present with disease in a range of extent from the recto-sigmoid only on to degrees of involvement including the entire colon. Initially, patients treated medically may be started on non-specific anti-inflammatory medications, most commonly mesalamine (5-ASA). Non-responders to a trial of medications may then be escalated in their therapy with cytotoxic or biologic medications. This "step-up" approach typically using mesalamine to treat active UC, is associated with clinical treatment failures in 60% of patients with moderate UC, compared to 80% treated with placebo. Moreover, a clinical response favoring doses of mesalamine greater than 2.5 grams per day has not been clearly shown despite clinical practice to the contrary.

Since biologics are associated with significantly increased costs compared to oral anti-inflammatory drugs, the early identification of patients who do not respond to mesalamine or conversely, who would respond to other therapies is important. The "step-up" medication strategy currently used does not take gender difference into consideration nor the locations of the disease within the colon. The same drug intervention strategy is applied to almost all UC patients, which is believed to be one of the key factors responsible for the high clinical treatment failure.

Numerous systems have been developed for inflammatory bowel disease (IBD) biomarkers including the use of fecal calprotectin and lactoferrin proteins for identifying patients with inflammatory bowel disease (IBD), assessing disease severity and for predicting relapses; the use of serum anti-*Saccharomyces cerevisiae* antibody (ASCA) and perinuclear antoneutriphil cytoplasmic antibody (pANCA) biomarkers to differentiate Crohn's Disease (CD) from UC; and the use of serum anti-OmpC IgA anti-CBir1 biomarkers with ASCA and other biomarker assays for IBD diagnosis as well as UC and CD differentiation. IBD disease biomarkers including anti-GM-CSF antibody, CD11b, TNF-a, CRP, aldo-keto reductase family 1 B10 (AKR1B10), perforin, NF-kB, CXC-chemokines, aquaporins, kinesins, adaptor protein-1 (AP-1), C5a, IL-2R, integrins, HCC-4, IL-7, MCP-1, MSP protein, IL-11, G-CSF, adrenoreceptors, ST2, E-cadhein, KC, IL-12123p40, IL-17, chlorotyrosine, PAP/REG3, MIF, DMBT1, LCN2, IL-22, haptoglobin, CCL20, IL-6, IL-33, CAP37, E4A (UBE4A), CXCL16, resistin, apolipoprotein A-IV, beta-defensin, NOD2/CARD15, NODUCARD4, toll-like receptors (TLR) 2 and 4, leptin, adiponectin, IL-10, DPP-IV, and CXCR4 have also been identified. Such biomarkers have been used for determining the responsiveness of steroid and biological treatments. However, until now, there have been no method or system developed for determining the responsiveness of a patient to mesalamine for the treatment of active UC.

As previously stated, one of the first lines of conventional UC clinical treatment is the use of mesalamine (5-ASA). However, the efficacy of mesalamine in active UC is only about 30-40%. UC pathophysiology and factors that influence the response to mesalamine treatment are not well known. The identified significant differences in protein profiling from different genders and anatomic colitis locations demonstrate that UC is a complicated disease.

Another problem with regard to the treatment of IBD is that diagnosis of an IBD patient can take some time and the "gold standard" for diagnosis is colonoscopy and verification through histopathology. Patients may bide their time and live with symptoms prior to their colonoscopy. During this period of unknown inflammatory damage can be done to the intestine and this cannot be reversed. Further, for the past several decades treatment protocols were based on the idea of therapeutic escalation. Patients were started on therapies with lower risk and side effects. If these therapies did not work (typically a 12-week period) therapy was escalated to others including the biologics. During this period of therapeutic trial and error, patients would continue to have symptoms and disease would progress.

In 2005, the Israeli military looked at possible serum markers using identified military personnel who had already been diagnosed with IBD and attempted to identify preclinical serums. The markers that were identified were the anti-*Saccharomyces cerevisiae* (ASCA) IgA, ASCA IgG antibodies and pANCA. They found that ASCA was detected in 31% of Crohn's patients with an average of 38 months, within a range of 20-77 months, prior diagnosis. pANCA was detected in 25% of UC patients prior to diagnosis, although their cohort was small. In 2012, using a European Prospective Investigation into Cancer and Nutrition (EPIC) study, investigators retrieved preclinical serum samples that were again tested with ASCA igG, ASCA igA, pANCA and also added other anti-bacterial Military Serum Bank, an investigation was conducted that further expanded the microbiota directed antibody panel of ASCA igG, ASCA igA, anti OmpC, anti-CBir1 with addition of anti-A4-Fla2 and anti-FlaX. One hundred military personnel and preclinical diagnostic samples were reviewed. It was found that that at least one of the anti-microbial antibodies could be detected up to a median of 6 years (range 5.6-8.2) prior to diagnosis. Patients with more complicated disease at time of diagnosis had detection of a greater number of anti-microbial antibodies in their sera. Also, in 2016 a study using the Nurses' Health Study 1 and II looked at circulating iL-6 and CRP. The multivariable-adjusted logistic regression models showed that the pre diagnostic sample highest plasma iL-6 concentrations were associated with an odds ratio (OR) of 2.82 for CD and OR of 1.79 for UC.

Accordingly, it would be beneficial to identify serum markers that are associated with pre-clinical diagnoses of IBD and whereby individuals that have a high risk of developing IBD can be identified and an effective therapy can be administered to such individuals thereby reducing inflammatory damage and providing a more effective treatment that is safer and potentially more effective for the particular individual.

SUMMARY OF THE INVENTION

The process and system of the subject invention is directed to a more effective, individual based treatment regimen which is built using clinical identified target biomarkers. In a preferred embodiment of the invention, the biomarkers identified herein establishes a foundation of UC target biomarkers associated with gender differential responses to mesalamine, and includes panels identifying protein target biomarkers that distinguishes mesalamine response differences between genders. Accordingly, the subject invention is directed to a process and system for determining the efficacy of mesalamine for patients being treated for various UC conditions. The subject invention is also directed to a process and system for developing effective strategies for the treatment of patients suffering from UC and to new, safe, effective, and potentially gender and colitis location dependent therapeutics.

Preferred embodiments of the subject invention are a process and a system that utilizes gender and disease locations to effectively develop new diagnostics and diagnostics standards for UC therapeutic strategies.

Another preferred embodiment of the subject invention utilizes gender and disease locations to permit personalized clinical UC medication regimens based on an individual patient's biomarker profiles.

Another preferred embodiment of the subject invention operates to identify mesalamine non-responders at a relatively early stage of UC using one or more panels of target biomarkers which allows for the development of a clinical medication approach having greater mesalamine efficacy.

Another preferred embodiment of the subject invention operates to identify mesalamine non-responders at a relatively early stage of UC using one or more panels of target biomarkers which allow faster and effective disease control with alternative treatments.

A preferred embodiment of the invention the panel is for male and female pancolitis and extensive colitis and comprises one or more target biomarkers selected from a list consisting of GSTM1, IL13, RETN and Histone H2a autoantibody.

Another preferred embodiment of the invention the panel is for female left sided colitis and comprises one or more target biomarkers selected from a list consisting of antibody to L. donovani, antibody to HTCLV1/2, and HSP90alpha autoantibody.

Another preferred embodiment of the invention the panel is for male left sided colitis and comprises one or more target biomarkers selected from a list consisting of APOA1, PRL, HSP 71 autoantibody and IgA.

Another preferred embodiment of the invention the panel is for female proctosigmoiditis and comprises one or more target biomarkers selected from the list consisting of CCL22 and antibody to cholera toxin.

Another preferred embodiment of the invention the panel is for male proctosigmoiditis and comprises one or more target biomarkers selected from the list consisting of ILRN and CD40 LG.

A preferred embodiment of the invention, the identified target biomarkers are gender dependent biomarkers.

Another preferred embodiment of the invention the identified target biomarkers are effective for predicting efficacy of mesalamine patients with pancolitis and extensive colitis.

Another preferred embodiment of the invention the identified target biomarkers are effective for predicting efficacy of mesalamine 2.4 g and 4.8 g daily therapy, given for 6 weeks to female and male patients with pancolitis and extensive colitis, and are selected from a panel comprising a list having one or more target biomarkers consisting of Model 1: GSTM1, IL13 and Histone H2a autoantibody and Model 2: Histone H2A autoantibody and RETN target biomarkers.

Another preferred embodiment of the invention the identified target biomarkers are effective for predicting the efficacy of mesalamine 2.4 g and 4.8 g daily therapy, given for 6 weeks for female patients with left-sided colitis, and are selected from a panel comprising a list one or more target biomarkers consisting of antibody to L. donovani, antibody to HTCLV 1/2, HSP90 alpha autoantibody target biomarkers.

Another preferred embodiment of the invention the identified target biomarkers are effective for predicting the efficacy of mesalamine 2.4 g and 4.8 g daily therapy, given for 6 weeks for male patients with left-sided colitis, and are selected from the panel comprising a list of one or more target biomarkers consisting of HSP 71 autoantibody, IgA, APOA1 and PRL target biomarkers.

Another preferred embodiment of the invention the identified target biomarkers are effective for predicting the efficacy of mesalamine 2.4 g and 4.8 g daily therapy, given for 6 weeks for female patients with proctosigmoiditis and are selected from the panel comprising a list of one or more target biomarkers consisting of CCL22, and antibody to cholera toxin.

Another preferred embodiment of the invention the identified target biomarkers are effective for predicting the efficacy of mesalamine 2.4 g and 4.8 g daily therapy, given for 6 weeks for male patients with proctosigmoiditis, and are selected from a panel comprising a list of one or more target biomarkers consisting of IL1RN, and CD40L.

A preferred embodiment of the invention is a process for predicting a patient's response to mesalamine for the treatment of ulcerative colitis (UC), the process comprises the steps of: identifying a patient diagnosed with UC; determining the location of the ulcerative colitis; obtaining a blood sample from the patient; using the sample to form a blood component; selecting a panel having one or more target biomarkers for the diagnosed UC, location and gender of the patient; using the blood component to make a determination as to the existence and quantity of one or more of the target biomarkers in the blood component; and using the determination to create an outcome that predicts the effectiveness of mesalamine treatment for the patient.

In a preferred embodiment of the invention the panel comprises levels of one or more target biomarkers selected from the list consisting of GSTM1, IL13, RETN and Histone H2a autoantibody effective for use in creating outcomes for male and female patients having pancolitis and extensive colitis.

In a preferred embodiment of the invention the panel comprises levels of one or more target biomarkers selected from the list consisting of antibody to *L. donovani*, antibody to HTCLV 1/2 and HSP90alpha autoantibody effective for use in creating outcomes for female left sided colitis.

In a preferred embodiment of the invention the panel comprises levels of one or more target biomarkers selected from the list consisting of APOA1, PRL, HSP 71 autoantibody and IgA effective for use in creating outcomes for male left sided colitis.

In a preferred embodiment of the invention the panel comprises one or more target biomarkers selected from the list consisting of CCL22 and antibody to cholera toxin effective for use in creating outcomes for female proctosigmoiditis.

In a preferred embodiment of the invention the panel comprises one or more target biomarkers selected from the list consisting of ILRN and CD40 LG effective for use in creating outcomes for male proctosigmoiditis.

In a preferred embodiment of the invention one or more panels are effective for predicting efficacy of mesalamine patients with pancolitis and extensive colitis.

Another preferred embodiment of the invention is a process for defining specific UC disease biomarkers as to gender and colitis locations comprising the steps of: obtaining a sample from the patient; using the sample to form a blood component, such as a serum, identifying one or more target biomarkers from the blood component and the levels of the identified target biomarkers, and using the levels of the identified target biomarkers to create an outcome that diagnoses mild-to-moderate ulcerative colitis disease.

In a preferred embodiment of the invention the process further comprises the step of using the panel and the levels and/or the change in levels of the one or more target biomarkers to develop novel UC therapeutics as new drug targets or as means to identify new drug targets or as means to screen new drug therapeutics.

A preferred embodiment of the invention is a process for predicting a patient's response to mesalamine for the treatment of ulcerative colitis (UC), the process comprises the steps of identifying a patient diagnosed with UC, determining the location of the UC, obtaining a first blood sample from the patient, mixing the blood sample with one or more separators to create a first blood component, selecting a panel, wherein the panel identifies one or more target biomarkers for the location of the UC and the gender of the patient, determining the level of each of the one or more target biomarkers in the first blood component, making a first comparison of the levels of the one or more target biomarkers in the first blood component to levels in a reference, and using the first comparison to create an outcome predicting the effectiveness of mesalamine treatment for the patient.

A preferred embodiment of the invention is a process for the treatment of ulcerative colitis (UC), the process comprises the steps of identifying a patient diagnosed with UC, determining the location of the UC, obtaining a first blood sample from the patient, creating a blood component devoid of red and white blood cells by mixing the first blood sample with one or more separators, selecting a panel based on the location and gender of the UC wherein the panel identifies one or more target biomarkers, making a determination of the existence and level of the one or more of the identified target biomarkers in the first blood component, administering a treatment to the patient for the UC, obtaining a second blood sample from the patient and mixing the second blood sample with one or more separators to create a second blood component, determining the level of each of the one or more target biomarkers in the second blood component, making a second comparison of the levels of the one of more target biomarkers in the second blood component to the levels of the one or more target biomarkers in the first blood component, and using the second comparison to evaluate the effectiveness of the treatment.

In a preferred embodiment of the invention the process further comprising the steps of identifying one or more compounds or proteins that effect, produces, or modifies one or more of the identified target biomarkers, and creating a treatment for the UC disease wherein such treatment is based on one or more of the identified compounds or proteins.

In another preferred embodiment of the invention further comprising the steps of identifying changes in one or more of the target biomarkers caused by one or more compounds or proteins and using the identified changes to analyze the disease mechanism of the type of UC being evaluated.

A preferred embodiment of the invention is a process for predicting a patient's response to mesalamine for the treatment of ulcerative colitis (UC), the process comprises the steps of: identifying the location of the UC, obtaining a blood sample from the patient diagnosed with the UC, forming a blood component by mixing the blood sample with one or more separators, selecting a panel identifying one or more target biomarkers based on the location and gender of the patient, using the blood component to make a determination as to the existence and quantity of one or more of said target biomarkers in the blood component, and using the determination to create an outcome that predicts the effectiveness of mesalamine treatment for the patient.

In a preferred embodiment of the invention the one or more separators are selected from the list consisting of an EDTA coated tube, and/or a Heparin coated tube, and/or a Citrate coated tube.

In a preferred embodiment of the invention the one or more separators are anticoagulants.

Another preferred embodiment of the invention is a process of identifying individuals that may have or have a greater risk of developing, IBD, Crohn's disease or Ulcerative Colitis prior to having physical symptoms.

A preferred embodiment of a process of determining if an individual is at risk of developing inflammatory bowel disease (IBD) prior to diagnosis of IBD comprises the steps of: identifying an individual that should be tested; obtaining a first blood sample of the individual; forming a blood component by mixing the blood sample with one or more separators, using the blood component to make a determination as to the existence and quantity of one or more of the target biomarkers in the blood component, selecting a panel of predictive target biomarkers; examining the blood component sample to obtain a level of each predictive target biomarker listed on the panel of predictive target biomarkers; determining the total level of protein in the sample; selecting a prediction logistic regression model and using the logistic regression model and the levels of each predictive target biomarker and the total level of protein in the blood sample to calculate a risk value; determining if the risk value is above or below a cut-off value for the selected prediction logistic regression model; wherein if the risk value is greater than the cut-off value, the process includes the step of administering a therapy to reduce the risk of developing IBD; and wherein if the risk value is below the cut-off value the process includes the step of administering a therapy to monitor the individual for detecting an increase in the risk of developing IBD.

In a preferred embodiment the process of determining if an individual is at risk of developing inflammatory bowel disease (IBD) prior to diagnosis of IBD includes the steps of: selecting a panel of predictive target biomarkers for use in determining the risk of the individual developing Crohn's disease; taking a blood sample from the individual and examining the blood sample to obtain a level of each predictive target biomarker listed on a panel of predictive target biomarkers for use in determining the risk of the individual developing Crohn's disease; selecting a prediction logistic regression model for use in determining the risk of the individual developing Crohn's disease and using the logistic regression model and the levels of each predictive target biomarker listed on the panel of predictive target biomarkers for use in determining the risk of the individual developing Crohn's disease and the total level of protein in the blood sample to calculate a risk value for developing Crohn's disease; determining if the risk value for developing Crohn's disease is above or below a cut-off value for the prediction logistic regression model for use in determining the risk of the individual developing Crohn's disease; wherein if the risk value for developing Crohn's disease is greater than the cut-off value for the prediction logistic regression model for use in determining the risk of the individual developing Crohn's disease, the process includes the step of administering a therapy to reduce the risk of developing Crohn's disease; and wherein if the risk value for developing Crohn's disease is below the cut-off value for the prediction logistic regression model for use in determining the risk of the individual developing Crohn's disease, the process includes the step of administering a therapy to monitor the individual for detecting an increase in the risk of developing Crohn's disease.

In a preferred embodiment the process of determining if an individual is at risk of developing inflammatory bowel disease (IBD) prior to diagnosis of IBD includes the steps of: selecting a panel of predictive target biomarkers for use in determining the risk of the individual developing ulcerative colitis (UC); taking a blood sample from the individual and examining the blood sample to obtain a level of each predictive target biomarker listed on the panel of predictive target biomarkers for use in determining the risk of the individual developing UC; selecting a prediction logistic regression model for use in determining the risk of the individual developing UC and using the logistic regression model and the levels of each predictive target biomarker listed on the panel of predictive target biomarkers for use in determining the risk of the individual developing UC and the total level of protein in the blood sample to calculate a risk value for developing UC; determining if the risk value for developing UC is above or below a cut-off value for the prediction logistic regression model for use in determining the risk of the individual developing UC; wherein if the risk value for developing UC is greater than the cut-off value for the prediction logistic regression model for use in determining the risk of the individual developing UC disease, the process includes the step of administering a therapy to reduce the risk of developing UC; and wherein if the risk value for developing UC is below the cut-off value for the prediction logistic regression model for use in determining the risk of the individual developing UC, the process includes the step of administering a therapy to monitor the individual for detecting an increase in the risk of developing UC.

In a preferred embodiment of the invention the process for determining the risk of an individual developing IBD includes the steps of identifying an individual that should be tested, obtaining a blood sample of the individual and examining the blood sample to identify one or more predictive target biomarkers and obtaining a level of the one or more identified predictive target biomarkers in the sample. A risk value is then created for the individual based on a ratio of the level of one or more identified predictive target biomarkers to the total amount of protein in the blood sample and taking into account any relationships between certain identified predictive target biomarkers. The process further includes the steps of obtaining an outcome that identifies the risk value of the individual indicating if the individual has a low, moderate or high risk of developing IBD (or Crohn's disease or ulcerative colitis). Depending on the risk level of the individual, a therapy may be administered prior to symptoms of IBD (or Crohn's disease or ulcerative colitis) appearing.

In a preferred embodiment of the invention the process one it is determined that the individual has a moderate or high risk of developing IBD (the risk value is above the cut-off value), the process includes the step of predicting the effectiveness of mesalamine treatment for the individual.

In a preferred embodiment of the invention, an individual identified as having a moderate or high risk of developing IBD (or Crohn's disease or ulcerative colitis) the process includes the step of administering a therapy that includes regulating the individual's diet to reduce the likelihood of developing IBD or Crohn's disease or ulcerative colitis.

In another preferred embodiment of the invention if an individual has been identified as having a moderate or high risk of developing IBD (Crohn's disease or ulcerative colitis), the process includes the step of using a blood sample to identify other target biomarkers to predict the efficacy of using mesalamine therapy.

In a preferred embodiment the predictive target biomarkers for use in determining the risk of a patient developing IBD (with environmental change and/or impactful stress of the individual considered and not considered), are selected from a list comprising the predictive target biomarkers of ACE (Angiotensin converting enzyme), CRP (C—reactive protein), CSF3 (Granulocyte colony stimulating factor), HP (Haptoglobin), sICAM1 (Soluble Intracellular adhesion molecule 1), RETN (Resistin), pANCA (auto antibody to Myeloperoxidase (MPO)), SCL-70 (auto-antibody to DNA Topoisomerase 1) and Anti-Tetanus toxoid IgG antibody (Tetanus Toxoid).

A preferred embodiment of the invention the process uses a first prediction logistic regression model to create a prediction outcome indicating the risk (likelihood) of an individual developing IBD without considering environmental change and/or impactful stress deployment of the individual.

In a preferred embodiment of the invention a first prediction panel comprises protein predictive target biomarkers of HP, GCSF, RETN, CRP, sICAM and antibody target biomarkers antibody to tetanus toxoid and identifies the relationships of sICAM×HP, GCSF×CRP and GCSF×RETN.

In a preferred embodiment of the process of predicting the risk of an individual developing IBD (without taking into account environmental change and/or impactful stress of the individual) uses a first prediction logistic regression model of: Log $(p/1ip)$=−641.8833706+71.65755693×Haptoglobin−41.87442414×GCSF−45.27490174×RETN−16.22723673×CRP−1.029456032×Antibody TT+14.476981343×sICAM+5.667294456×(sICAM×Haptoglobin)−0.80715758−(GCSF×CRP)−2.288843531×(GCSF×RETN).

A preferred embodiment of the invention the process uses a second prediction logistic regression model to create a prediction outcome indicating the risk (likelihood) of an individual developing IBD with consideration of Environmental Change and/or Impactful Stress of the individual.

In a preferred embodiment of the invention a second prediction panel comprises protein predictive target biomarkers of sICAM, GCSF, HP, CRP, RETN and antibody target biomarkers antibody to tetanus toxoid.

In a preferred embodiment of the process of predicting the risk of an individual developing IBD (with consideration of the Environmental Change and/or Impactful Stress of the individual) uses a second prediction logistic regression model of: Log (p/1ip)=1101.571616−0.813305575×(Environmental Change and/or Impactful Stress)−104.1257102×sICAM−62.63858365×GCSF−5.604142451×sICAM×GCSF+65.611507602×HP+5.107130532×sICAM×HP−36.81637743×TT−1.711888269×GCSF×TT+0.767135503×CRP+1.770741857×RETN.

A preferred embodiment of the invention the process uses a third prediction logistic regression model to create a prediction outcome indicating the risk of an individual developing Crohn's disease.

In a preferred embodiment of the invention a third prediction panel comprises protein predictive target biomarkers of SCL70, AcE, RETN, CRP, GCSF and antibody target biomarkers antibody to tetanus toxoid (TT) and identifies the relationships of sICAM×RETN, GCSF×TT.

In a preferred embodiment of the process of predicting the likelihood of an individual developing Crohn's disease uses a third prediction logistic regression model of: Log (p/1ip)=−174.4+171.2×SLC70−4.0×AcE−32.2×RETN+1.1×CRP+15.9×GCSF−57.4−TT+11.6×(sICAM×RETN)−2.7×(GCSF×TT).

A preferred embodiment of the invention comprises a fourth prediction panel comprises protein predictive target biomarkers for use in creating a prediction outcome of the risk of an individual developing ulcerative colitis (UC).

In a preferred embodiment of the invention a fourth prediction panel comprises protein predictive target biomarkers of HP, SICAM1 and RETN, and identifies the relationship of sICAM1×HP.

In a preferred embodiment of the method of predicting the likelihood of an individual developing ulcerative colitis uses a fourth prediction logistic regression model of: Log (p/1−p)=221.7+2.2×Resistin+15.1×sICAM+61.5×Haptoglobin+4.9×(sICAM×Haptoglobin).

A preferred embodiment of the process of determining the likelihood of an individual having IBD (with or without consideration of Environmental Change and/or Impactful Stress of the individual), Crohn's disease or ulcerative colitis comprises the steps of: identifying an individual that should be tested for IBD, Crohn's disease or ulcerative colitis (collectively referred to as "Disease") prior to showing signs of the Disease; obtaining a first blood sample from the individual; selecting one or more predictive target biomarkers from a prediction panel for the Disease; determining the level of the selected one or more predictive target biomarkers in the first blood sample; determining the level of total amount of protein in the first blood sample and determining a ratio of the level of each selected predictive target biomarker to the total amount of protein in the blood sample; using a prediction logistic regression model to determine a risk value of the individual developing the Disease; determining if the risk value is above or below a cut-off value; and make a prediction outcome indicating the risk of the individual developing the Disease.

In a preferred embodiment of the invention if the risk value is above the cut-off value the process includes the steps of creating a treatment protocol based on the individual's profile.

In a preferred embodiment of the invention the process of treating an individual having a high risk of developing IBD further comprises the step of using the prediction panel(s) and changes in risk value(s) of the individual or individuals being treated for IBD prior to symptoms observed to develop novel IBD therapeutics as new drug targets or as means to identify new drug targets or as means to screen new drug therapeutics to reduce the risk of individuals developing IBD or to slow down the progression of the IBD.

In a preferred embodiment of the invention the process further comprising the steps of identifying one or more compounds or proteins that effect, produces, or modifies one or more of the predictive target biomarkers that reduces the risk of an individual developing IBD, and creating a treatment for reducing the risk of an individual developing IBD or to slow down the progression of the IBD wherein such treatment is based on one or more of the identified compounds or proteins.

Other embodiments, advantages and objects of the invention will be apparent from the following description and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIG. 3 illustrates specific biomarker panels for a patient diagnosed with UC based on the gender of the patient and the location of the UC;

FIGS. 4A and 4B shows Table 1 displaying significant univariate analytes with a p value of less than 0.2 which were used to build the final biomarker multivariate model for success or failure of male/female pan/extensive colitis and also shows distribution of proteins that predict success or failure of 5ASA within subgroups;

FIG. 5 shows Table 2 displaying descriptive ranges of location and gender specific biomarkers;

FIG. 6 shows Table 3 displaying predictive models for location and gender;

FIG. 7 shows Table 4 displaying significant univariate analytes with p values of less than 0.2 which were used to build the final biomarker multivariate model for success or failure of female left-sided colitis UC patients;

FIG. 8A and FIG. 8B shows Table 5 displaying significant univariate analytes with p vales of less than 0.2, which were used to build the final biomarker multivariate model for success or failure of male left-sided ulcerative colitis patients;

FIG. 9 shows Table 6 displaying significant univariate analytes with p value of less than 0.2, which are used to build the final biomarker multivariate model for success or failure of proctosigmoiditis UC female patients;

FIG. 10 shows Table 7 displaying male proctosigmoiditis univariate analytes used for multivariate modeling;

FIG. 11 shows Table 8 displaying a list of target biomarkers for male locations of proctosigmoiditis, left-sided colitis and extensive/pancolitis that can be used for drug development, compound screening, diagnostics, and monitoring therapeutic responses;

FIG. 12 shows Table 9 displaying a list of target biomarkers for male locations of proctosigmoiditis, left-sides and extensive/pancolitis that can be used for drug development, compound screening, diagnostics, and monitoring therapeutic responses;

FIG. 13 shows Table 10 displaying the list of target biomarkers for male proctosigmoiditis, left-sided and pan/extensive that can be used for drug development, compound screening, diagnostics, and monitoring therapeutic responses;

FIG. 14 shows Table 11 displaying a list of target biomarkers for female locations of proctosigmoiditis, left-sided and extensive/pancolitis that can be used for drug development, compound screening, diagnostics, and monitoring therapeutic responses;

FIG. 15 shows Table 12 displaying a list of target biomarkers for female locations of proctosigmoiditis, left-sides and extensive/pancolits that can be used for drug development, compound screening, diagnostics, and monitoring therapeutic responses;

FIG. 16 shows Table 13 displaying the list of target biomarkers for female proctosigmoiditis, left-sided and pan/extensive that can be used for drug development, compound screening, diagnostics, and monitoring therapeutic responses;

FIG. 17 is a flow diagram of the general methodology of a preferred embodiment of the invention showing the process of creating an outcome that predicts the efficiency of an administered medication;

DETAILED DESCRIPTION OF THE INVENTION

Figure 1:
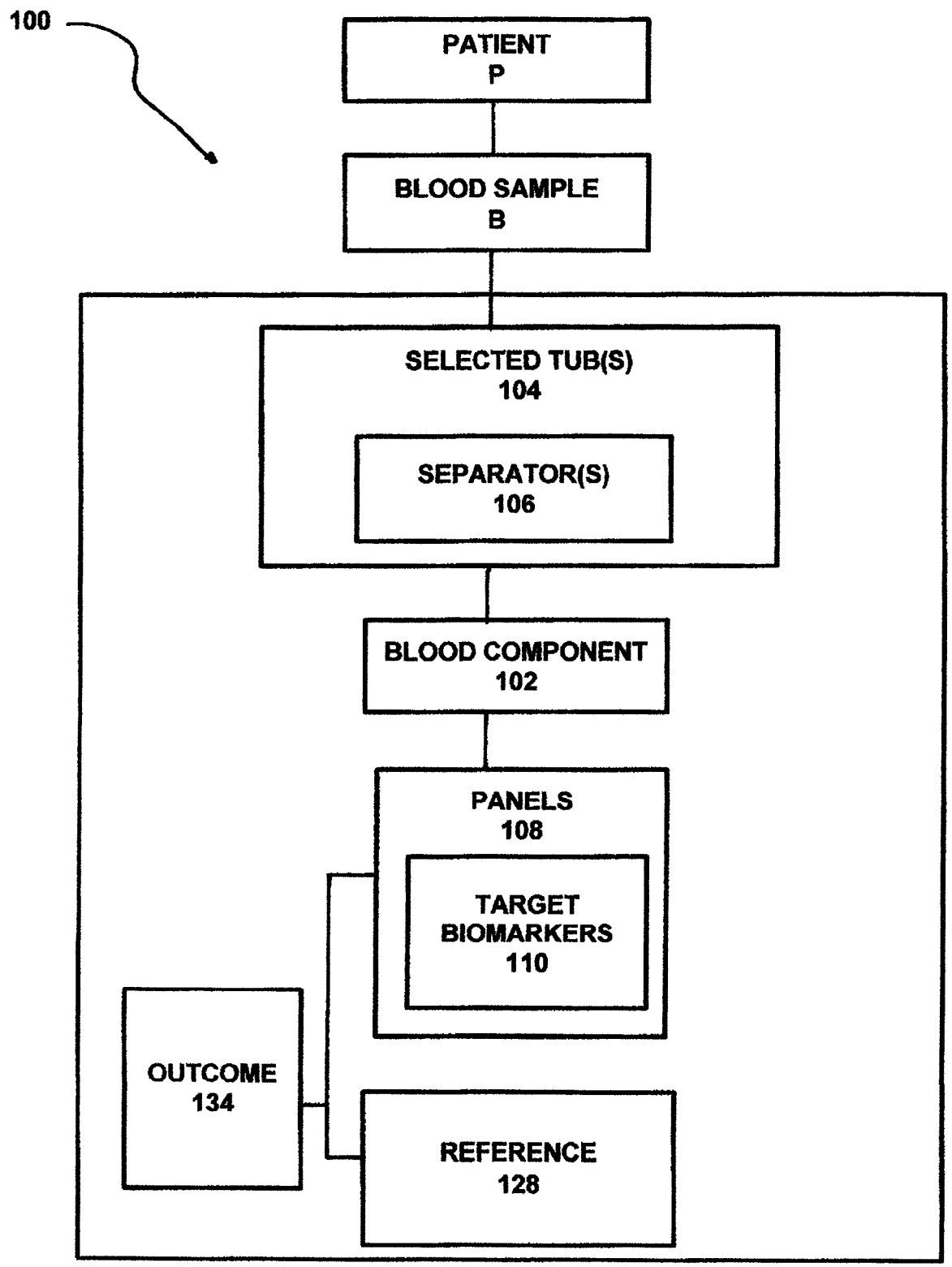
FIG. 1 is a schematic representation illustrating the system of the subject invention whereby a blood component comprising a blood sample from a patient diagnosed with a form of UC is mixed with one or more separators to form a blood component that is devoid of red and white blood cells, a panel identifying one or more target biomarkers based on gender and location of the UC, the blood component further comprises levels (quantity) of one or more target biomarkers, and a reference for comparing the levels of the target biomarkers for creating an outcome.

Using mesalamine to treat active UC is associated with clinical treatment failures in 60% of patients with moderate UC, compared to 80% of those treated with placebo. Due to the lack of understanding of disease pathophysiology, until now, mesalamine treatment did not take gender difference into consideration nor the locations of the disease within the colon. Patients, such as those with left-sided colitis and proctosigmoiditis are difficult to manage clinically. However, patients with proctosigmoiditis do not have greatly increased predilection to developing colon cancer. This is different from those patients with pancolitis and extensive colitis that have significantly higher risk of developing colon cancer. Therefore, it is desirable to have a process and system that are effective for use in specifically predicting mesalamine treatment responses for subgroups of patients having UC as well as for use in developing effective strategies for the treatment of patients suffering from UC as well as for developing new and effective therapeutics effective for the treatment of UC at different anatomic colon locations.

In a preferred embodiment, the subject invention comprises panels of protein biomarkers ("target biomarkers") that distinguish mesalamine response differences between genders and anatomic colitis locations. Using these panels of target biomarkers as described herein, mesalamine non-responders can be identified earlier. Further, using such panels of target biomarkers a new clinical medication process has been developed having greater efficacy and is faster and more effective for disease control while allowing for alternative treatments for the non-responders.

Preferably, the process or system of the subject invention comprise two categories of panels that identify target biomarkers based on their differences in utility. The first category of panels provides a list of identify target biomarkers that are gender dependent and operate to predict mesalamine treatment outcomes (success or failure) for mild-to-moderate UC patients. The method and system utilize the panels as unique tools allowing physicians to decide optimal personalized UC therapy strategies. The process and system further utilize different panels identifying target biomarkers for patients with colitis in different colonic locations.

The second category of panels provide a list of identified target biomarkers used for mild-to-moderate UC disease for specific genders at different colitis locations. The panels operate for determining and validating new UC drug targets. The panels comprise listings of identified target biomarkers that are used for new drug targets themselves, or are used in understanding UC mechanism and to determine or identify other molecules, proteins, and the like for new therapeutic targets. The panels identifying disease target biomarkers are also used as tools for screening UC therapeutic compounds, as well as for diagnosing mild-to-moderate UC.

First Category: Gender Dependent Target Biomarkers for Predicting Mesalamine Treatment Outcomes In a preferred embodiment, the system and process of the subject invention utilize a first category of gender dependent target biomarkers to create outcomes that predict the efficacy of mesalamine treatment (success or failure) on mild-to-moderate UC patients with different colitis locations (left-sided colitis, proctosigmoiditis, pancolitis, and extensive colitis).

Figure 2:
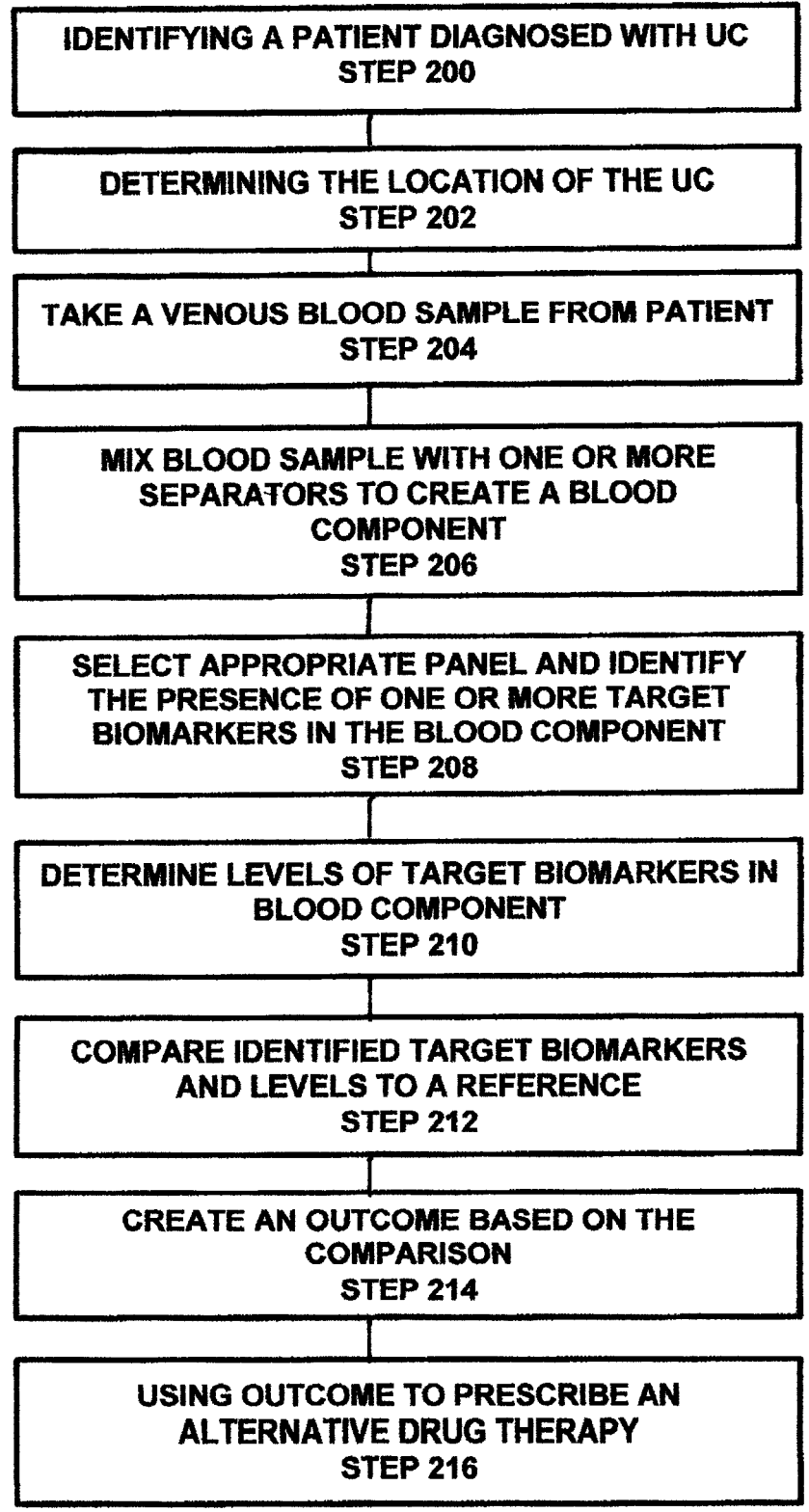
FIG. 2 is a flow diagram showing the general methodology of the process for predicting efficacy of mesalamine for patients being treated for a diagnosed UC condition.

As illustrated in FIGS. 1 and 2, the system 100 and process of the subject invention comprises identifying a patient P diagnosed with UC (step 200) and determining the location of the UC (step 202). A venous blood sample B is taken from the patient P (step 204) and a specified blood component 102, such as in the form of a serum or plasma, is created by mixing the blood sample B with one or more separators 106 (step 206). As used herein, the term "serum," unless otherwise stated, refers to both serum and plasma. In a preferred embodiment, the blood component 102 is in the form of a plasma (not a serum) and is created by placing the blood sample B into at least one selected tube 104 coated with or having one or more separators 106, such as an EDTA coated tube, and/or a Heparin coated tube, and/or a Citrate coated tube to create the specified blood component 102, such as an EDTA plasma, and/or a Heparin plasma, and/or a citrate plasma, respectively. Another preferred embodiment of the invention, the blood component 102 is in the form of a serum (not plasma) created and using a venous blood sample B drawn from a patient P into at least one selected tube 104 having one or more separators 106, such as physical serum separators (i.e. SST tubes). After the venous blood B is drawn into the selected tube 104 it is immediately inverted 3-5 times, so that the various serum separators 106 (anticoagulants), are mixed into the blood sample B creating the blood component 102 in the form of a serum (not plasma) devoid of red and white blood cells. Each of the one or more tubes 104 having the mixture of blood sample B and separators 106 is rested for up to 30-60 minutes at room temperature and then centrifuged at either room temperature or at 4-8° C. for 20 minutes at 1800-2000 rpm. For a blood component 102 in the form of a plasma, once the blood sample B is drawn into one or more of the tubes 104, the tubes are inverted 3-5 times to mix the blood sample with the separators 106 (EDTA and/or Heparin and/or Citrate) and centrifuged at either room temperature or at 4-8° C. for 20 minutes at 1800-2000 rpm. After centrifugation, the cells of the blood sample will pellet to the bottom of the tube or get separated physically by the separator and a purified blood component in the form of a serum or plasma is collected.

Referring to FIG. 3, the subject invention further utilizes one or more panels 108 identifying one or more target biomarkers 110. The one or more panels 108 preferably comprises a first panel 112 is shown and identifies gender dependent target biomarkers 110. Upon evaluation of statistical analysis data (p values, t values risk ratio, estimates and effect increments), the target biomarkers 110 identified in the first panel 112 were selected as being effective for use in predicting efficacy of mesalamine (2.4 g and 4.8 g daily therapy, given for six weeks) for female and male patients with pancolitis and extensive colitis and can be are used individually or in any combination for predicting mesalamine efficacy.

The one or more panels 108 preferably further comprises a second panel 116 identifying gender dependent target biomarkers 110 as shown and upon evaluation of statistical analysis data (p values, t values, risk ratio, estimates and effect increments), were selected as being effective for use in predicting efficacy of mesalamine (2.4 g and 4.8 g daily therapy, given for six weeks) for female patients with left-sided colitis and are used individually or in any combination for predicting mesalamine efficacy.

The one or more panels 108 preferably further comprises a third panel 120 identifying gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for male patients with left-sided colitis and are used individually or in any combination for predicting mesalamine efficacy.

The one or more panels 108 preferably further comprises a fourth panel 124 identifying gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for female patients with proctosigmoiditis and are used individually or in any combination for predicting mesalamine efficacy.

The one or more panels 108 preferably further comprises a fifth panel 128 of gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for male patients with proctosigmoiditis and are used individually or in any combination to predict mesalamine efficacy.

It should be understood that one aspect of the subject invention provides a process and system whereby panels of gender dependent target biomarkers are used as for predicting mesalamine treatment outcomes on mild- to moderate UC patients with different colitis locations (left-sided colitis, proctosigmoiditis, pancolitis and extensive colitis). Such outcome predictions can be made by comparing the levels of such target biomarkers in patients with a reference to determine if the levels (quantity) of target biomarkers are higher or lower than the levels disclosed in the reference. Such differences are then used to create outcomes predicting the effectiveness of mesalamine treatment for the patient. Having now generally described the invention, the same will be more readily understood through reference to the following examples which are provided by way of illustration, are not intended to be limiting of the present invention, unless specified.

Exemplary Illustrations of Preferred Embodiments

A. Use of Mesalamine Non-Responder Serum (or Plasma) Biomarkers in Personalized UC Clinical Practice Using mesalamine to treat active UC is associated with clinical treatment fails in 60% of patients with moderate UC, compared to 80% treated with placebo. Due to the lack of understanding of disease pathophysiology, until now conventional mesalamine treatments did not take gender difference into consideration nor the locations of the disease within the colon. The panels of the subject invention operate to identify protein target biomarkers and use such target biomarkers to create outcomes with regard to mesalamine response for patients based on the patient's gender and anatomic colitis locations. Accordingly, the panels identifying specific target biomarkers operate to allow users to identify mesalamine non-responders earlier. Further, using such panels new clinical medication approaches are administered that have greater efficacy and alternative treatments for non-responders can be administered at an earlier stage of the disease.

By way of a non-limiting example, the subject invention provides outcomes that predict mesalamine responses on pancolitis and extensive colitis UC patients. Referring to FIGS. 1 and 2, in a preferred embodiment of the invention the process includes the step of identifying a patient that has been diagnosed as having UC (step 200). The colonic colitis location is then determined (step 202) such as by colonoscopy as part of standard clinic procedures. A clinician obtains one or more blood samples B (step 204) and creates a blood component 102 (step 206), such as in the form of a serum, as described above, and using the appropriate panel 108 identifies non-responder target biomarkers 110 as disclosed hereinabove (step 208), determines the levels (quantity) of the target biomarkers in the blood component 102 (step 210) prior to treatment of this patient's active colitis and compares the levels with levels of a reference 128 (step 212). Table 1 (FIGS. 4A and 4B) shows significant univariate analytes with a p value of less than 0.2 which were used to build the final biomarker multivariate model (reference) for success or failure of male/female pan/extensive colitis in Tables 2 and 3 (FIGS. 5 and 6, respectively). Table 1 also shows distribution of proteins that predict success or failure of 5ASA within subgroups. In Tables 2 and 3 the mean, standard error and range reported are reported in pg/ml, ng/ml, or the MFI ratio for each valid biomarker. N total indicates the total number of subjects within a subgroup with observations for each protein. MFI ratio unit indicates the ratio of median fluorescence intensity (MFI) of target-specific, antigen-coupled microspheres to MFI generated by a negative control microsphere tested in each sample well. The levels of the target biomarkers are then compared to prescribed levels of a reference 128 as shown in Tables 2 and 3 (FIGS. 5 and 6, respectively), (step 212) and an outcome 134 is generated (step 214). In a preferred embodiment of the invention the outcome predicts the efficacy of mesalamine (2.4 g and 4.8 g daily therapy, given for six weeks for female and male patients with pancolitis and extensive colitis). For example, if the patient shows significant difference in levels of the specified mesalamine non-responder target biomarkers (for example, higher serum level of IL13 at baseline with a 1 pg/ml increase) then the outcome 134 will show that it is likely that the patient will not respond to the mesalamine treatment. It should be understood that Table 2 (FIG. 5) identifies statistically predictive serological biomarkers consisting of serum proteins, autoimmune antibodies and antibodies recognizing infectious agents are shown for models of success vs. failure of 5ASA in each of the 5 subgroups. Effect increment indicates the quantitative increment of each protein in pg/ml, ng/ml, MFI ratio unit, or 5ASA dosage associated with the regression estimate and risk ratio. MFI ratio unit indicates the ratio of median fluorescence intensity (MFI) of target-specific, antigen-coupled microspheres to MFI generated by a negative control microsphere tested in each sample well. The values are stated in ng or pg/ml of protein as detected by the Rules-based medicine platform. It should also be understood that Table 1 (FIGS. 4A and 4B) shows significant univariate RBM analytes with a p value of less than 0.2 used for predictive multivariate modeling in male/female Pancolitis/Extensive.

In a preferred embodiment, in addition to the above mentioned panels of target biomarkers that are generic to both male and female pancolitis and extensive colitis patients, additional comparisons may be made using panels of additional target biomarkers, such as comparing levels of female specific target biomarkers (CCL22, antibodies to Cholera toxin, *L. donovani*, HTCLV1/2 and autoantibody to HSP90 alpha) or levels of male specific target biomarkers may be used (IL1RN, CD40L, APOA1, PRL, IgA and autoantibody to HSP 71) as non-responder markers to determine if it is likely that this patient will not respond to mesalamine treatment. Consideration of an alternative drug therapy (such as anti-TNF molecules) is then made (step 216).

In another preferred embodiment of the invention as shown in Table 4 (FIG. 7), the subject invention provides a method and system for the prediction of mesalamine response on left-sided colitis UC female patients. Table 4 also shows significant univariate RBM analytes with p values of less than 0.2 used for multivariate and predictive modeling female left-sided colitis. In another non-limiting the method includes identifying a patient that has been diagnosed with left-sided colitis UC. Left-sided colitis is verified such as by colonoscopy as part of standard clinic procedures. It should be understood that for left-sided colitis, mesalamine is the common medication prescribed to the individual under current standard practice. Using the appropriate mesalamine non-responder target biomarkers identified hereinabove, a clinician runs one or more blood tests and obtains samples and creates a serum and identifies and determines the levels of one or more target biomarkers prior to treatment of the patient's active colitis. The levels of the target biomarkers are then be compared to levels or a reference, such as shown in Tables 2 and 3 (FIGS. 5 and 6, respectively), and an output is generated that predicts the efficacy of mesalamine (2.4 g and 4.8 g daily therapy, given for six weeks for male and female patients with left-sided colitis UC) is made. For example, if the patient shows significant difference in levels of the specified mesalamine non-responder target markers (for example MFI or protein level changes for antibody to *L. donovani*, Antibody to HTCLV1/2, HSP90alpha autoantibody for female patients with left-sided colitis, then a prediction is made that it is likely that the patient will or will not respond to the mesalamine treatment depending on the protein directionality outlined in Tables 2 and 3. Consideration of another drug therapy (such as anti-TNF molecules) could also be made at that time.

In another preferred embodiment of the invention, the subject invention includes a process and system for predicting mesalamine response on left-sided colitis UC male patients. Table 5 (FIG. 8) shows significant univariate analytes with p vales of less than 0.2, which were used to build the final biomarker multivariate model (reference) for success or failure of left-sided colitis UC male patients in Tables 2 and 3 (FIGS. 5 and 6, respectively). The process includes identifying a patient having UC, such as diagnosed with left-sided colitis UC. The condition and location are verified such as by colonoscopy as part of standard clinic procedures. It should be understood that for left-sided colitis, mesalamine is the common medication prescribed to the individual under current standard practice. Using the appropriate panel identifying mesalamine non-responder target biomarkers described hereinabove, a clinician runs one or more blood tests and obtains a blood sample using and creates a blood component, such as plasma or serum. The levels of the target biomarkers are determined prior to treatment of this patient's active colitis. The levels of the target biomarkers are compared to levels of a reference, such as shown in Tables 2 and 3 (FIGS. 5 and 6, respectively) and an outcome that predicts the efficacy of mesalamine, such as 2.4 g or 4.8 g daily therapy, given for six weeks for male and female patients with left-sided colitis UC, is made. For example, if the patient shows significant difference in levels of the specified mesalamine non-responder target markers (for example, MFI or protein level changes for antibody to *L. donovani*, Antibody to HTCLV1/2, HSP90alpha autoantibody for female patients and to HSP 71 autoantibody, IgA, APOA1 and PRL for male patients with left-sided colitis, then an outcome that predicts the likelihood that the patient will or will not respond to the mesalamine treatment is made depending on the protein directionality outlined in Tables 2 and 3. In a preferred embodiment the outcome further recommends an alternative drug therapy or regimen.

In another non-limiting example of the invention, the process and system operate to predict mesalamine response on proctosigmoiditis UC female patients is shown in Table 6 (FIG. 9). Table 6 also shows significant univariate analytes with p value of less than 0.2, which were used to build the final biomarker multivariate model (reference) for success or failure of proctosigmoiditis UC female patients in Tables 2 and 3 (FIGS. 5 and 6). The process includes identifying a patient that has been diagnosed with proctosigmoiditis UC. The proctosigmoiditis is verified such as by colonoscopy as part of standard clinic procedures. It should be understood that for proctosigmoiditis, mesalamine is the common medication prescribed to the individual in current standard practice. Using the appropriate mesalamine non-responder target biomarkers identified hereinabove, a clinician runs one or more blood tests and obtains a blood sample and creates a blood component, such as serum or plasma, and selects the proper panel and determines the levels of the target biomarkers prior to treatment of this patient's active proctosigmoiditis. The levels of the target biomarkers are then compared to levels of a reference, such as shown in Tables 2 and 3, and an outcome is generated that predicts the efficacy of mesalamine (such as for 2.4 g and 4.8 g daily therapy, given for six weeks for female and male patients with proctosigmoiditis). For example, if the patient shows significant difference in levels of the specified mesalamine non-responder target biomarkers (i.e. CCL22 and antibody to cholera toxin for females) then it is likely that the patient will not respond to the mesalamine treatment. In a preferred embodiment, the outcome includes an alternate drug therapy or regimen. Table 6 (FIG. 9) shows significant univariate analytes with a p value of less than 0.2, which were used to build the final biomarker multivariate model for success or failure of female proctosigmoiditis in Tables 2 and 3.

In another non-limiting example of the invention, as shown in Table 7 (FIG. 10), the subject invention is a process and system for predicting mesalamine response on male proctosigmoiditis UC patients. Table 7 also shows significant univariate analytes with p values of less than 0.2, which were used to build the final biomarker multivariate model (reference) for success or failure of proctosigmoiditis UC male patients in Table 2 and 3 (FIGS. 5 and 6, respectively). The process includes identifying a patient that has been diagnosed with proctosigmoiditis UC. The proctosigmoiditis is verified such as by colonoscopy as part of standard clinic procedures. It should be understood that for proctosigmoiditis, mesalamine is the common medication prescribed to the individual under current standard practice. Using the appropriate panel identifying mesalamine non-responder target biomarkers as described hereinabove, a clinician runs one or more blood tests and obtains a blood sample and creates a blood component, such as serum or plasma, and determines the levels of the target biomarkers prior to treatment of this patient's active proctosigmoiditis. The levels of the target biomarkers are then be compared to levels of a reference, such as shown in Tables 2 and 3 (FIGS. 5 and 6, respectively) and an outcome is generated that that predicts the efficacy of mesalamine (2.4 g and 4.8 g daily therapy, given for six weeks for male patients with proctosigmoiditis). For example, if the patient shows significant difference in levels of the specified mesalamine non-responder target biomarkers (for example, IL1RN, CD40L for males, then it is likely that the patient will or will not respond to the mesalamine treatment depending on the directionality of the protein test as listed in Table 3 (FIG. 6). Preferably, the outcome further includes an alternate drug therapy.

B. Use of Serum Target Biomarkers for Diagnosis and New Drug Development of Mild-To-Moderate UC Disease It should be understood that the target biomarkers identified in the panels are gender and colitis location specific UC disease target biomarkers. In another preferred embodiment of the invention, the panels are used for the early diagnosis of disease, localization of disease, the development of new personalized UC drugs, the measurement of the response to a drug treatment regimen or for assays for compound screening of therapeutics.

The following example illustrates the list of target biomarkers as shown in Tables 8-10 (FIGS. 11-13) for the male gender and Tables 11-13 (FIGS. 14-16) for the female gender that can be used for drug development, compound screening, diagnostics, location of disease and monitoring therapeutic responses. It should be understood to one skilled in the art that since pancolitis and extensive colitis at these colonic locations have a significantly greater risk of developing colon cancer than patients with disease limited to proctosigmotidis or left sided colitis, early diagnosis of the disease as well as effective therapeutics is highly desirable. The target biomarkers identified herein in Tables 8-10 (FIGS. 11-13) and Tables 11-13 (FIGS. 14-16) are gender and colitis location specific UC disease biomarkers that can be applied as targets of the early diagnosis of disease, for the development of new personalized UC drugs, further verification of disease location diagnosis, for the measurement of the response to drug therapy, or for assays for compound screening therapeutics.

In another preferred embodiment of the invention as shown in FIG. 17 the subject invention uses target biomarkers for patients with a particular UC condition. The subject invention provides a process whereby (such as in a non-limiting illustrative example, where the patient is diagnosed with pancolitis and extensive colitis) target biomarkers verify disease location and are used for drug targets, medication screening, diagnostics, and for monitoring therapeutic responses. In this particular example, the process includes identifying the gender of the patient that has been diagnosed with UC (step 300) and verifying the location of the UC such as by colonoscopy as part of standard clinic procedures (step 302). A clinician runs one or more blood tests and obtains a first blood sample (step 304) and creates a first blood component, such as a serum, by mixing the first blood sample with one or more separators (step 306). The appropriate panel for the patient's gender and UC is selected that identifies one or more target biomarkers (step 308) and the levels of the target biomarkers prior to treatment of this patient's UC, such as active left-sided colitis, is determined (step 310). Medication is then given to the patient (step 312). A clinician runs additional blood tests and obtains a second blood sample(s) (step 314) and creates a second blood component (step 316), such as a serum. The levels of the target biomarkers in the second blood component are then compared to levels of target biomarkers of a reference (step 318), such as for the particular colitis. In a preferred embodiment, as shown in FIG. 17, the reference comprises levels of the target biomarkers found in the first blood component.

In another non-limiting example, the reference comprises the levels of the target biomarkers shown in Tables 2 (FIG. 5) and 10 (FIG. 13) for male subject colitis and Tables 2 (FIG. 5) and 13 (FIG. 16) for female subject colitis. Depending on the changes in the levels of the target biomarkers (changes from levels found in the first blood component to levels found in the second blood component), an outcome is created (step 316) that predicts the efficacy of the administered medication. For example, if the patient shows significant difference in levels of the target biomarkers it can be determined that the proscribed medication is improving the patient's condition or is not effective for improving the patient's condition. It should now be apparent to one skilled in the art that the subject invention allows for the development of new personalized UC drugs, for the measurement and monitoring of a patient's response to drug therapy, or for assays for compound screening therapeutics.

In another non-limiting example the process includes identifying a male or female patient that has been diagnosed with left-sided colitis. The left-sided colitis is verified such as by colonoscopy as part of standard clinic procedures. A clinician runs one or more blood tests and obtains a first blood sample and creates a first blood component, such as a serum, and determines the levels of target biomarkers prior to treatment of this patient's active left-sided colitis. Medication is then given to the patient. A clinician runs additional blood tests and obtains an additional blood sample and creates a second blood component, such as a serum. The levels of the target biomarkers are then compared to levels of a reference, such as for an example as shown in Tables 2 (FIG. 5) and 10 (FIG. 13) for a male and Tables 2 (FIG. 5) and 13 (FIG. 16) for a female with pancolitis and extensive colitis and depending on the changes in the levels of the target biomarkers, an outcome can be created that predicts the efficacy of the administered medication. For example, if the patient shows significant difference in levels of the target biomarkers it can be determined that the proscribed medication is improving the patient's condition or not.

The following non-limiting example illustrates a list of target biomarkers for left-sided colitis, as shown in Table 8 (FIG. 11) for a male and shown in Table 11 (FIG. 14) for a female, that can be used for drug development, compound screening, diagnostics, and monitoring therapeutic responses. In a preferred embodiment the process includes identifying a patient that has been diagnosed with a particular UC, in this example left-sided colitis. The left-sided colitis is verified such as by colonoscopy as part of standard clinic procedures. A clinician runs one or more blood tests and obtains a blood sample and creates a blood component, such as a serum, and determines the levels of target biomarkers prior to treatment of this patient's active left-sided colitis. Medication is then given to the patient. A clinician obtains a second blood sample and creates a second blood component, such as a serum. The levels of the target biomarkers in the first blood component are then compared to levels of target biomarkers in the second blood component (reference), and depending on the changes in the levels of the target biomarkers, an outcome can be created that predicts as to the efficacy of the administered medication is made. For example, if the patient shows significant difference in levels of the target biomarkers it can be determined that the proscribed medication is improving the patient's condition or not.

The following non-limiting example illustrates the list of target biomarkers for proctosigmoiditis, such as shown in Table 9 (FIG. 12) for a male and Table 12 (FIG. 15) for females, that can be used for drug development, compound screening, diagnostics, and monitoring therapeutic responses. In a preferred embodiment the process includes identifying a particular UC condition. In this illustrative example the patient has been diagnosed with proctosigmoiditis. The proctosigmoiditis is verified such as by colonoscopy as part of standard clinic procedures. A clinician runs one or more blood tests and obtains a first blood sample and creates a blood component, such as a serum, and determines the levels of target biomarkers prior to treatment of this patient's active proctosigmoiditis. Medication is then given to the patient. A clinician runs additional blood tests and obtains a second blood sample and creates a blood component, such as a serum. The levels of the target biomarkers in the first blood component are then compared to levels of the second blood component (reference), and depending on the changes in the levels of the target biomarkers, an outcome can be created that predicts the efficacy of the administered medication. For example, if the patient shows significant difference in levels of the target biomarkers it can be determined that the prescribed medication is improving the patient's condition or not.

It should now be apparent to one skilled in the art that the present invention provides a process and system whereby panels of target biomarkers are used for risk assessment and predict with a high degree of reliability the treatment outcome with respect to a patient expressing higher than normal levels of targeted biomarkers and thus provides substantive value in various aspects of patient care management. It should also now be apparent to one skilled in the art that the process and system of the subject invention prevents or reduces the likelihood of treatment using ineffective medications as well as reducing the possibility of the patient experiencing un-necessary side effects of mesalamine as well as the potential delay in clinical recovery due to use of ineffective drug choice. Further, it should be understood that the process and system reduce a delay in in clinical recovery that could be clinically significant since pancolitis patients have great risk in developing colon cancer. Accordingly, the use of the process and system (of personalized medicine for patients with UC) of the subject invention is very beneficial to the patient, the prescribing practitioner, and insurance companies.

Figure 18:
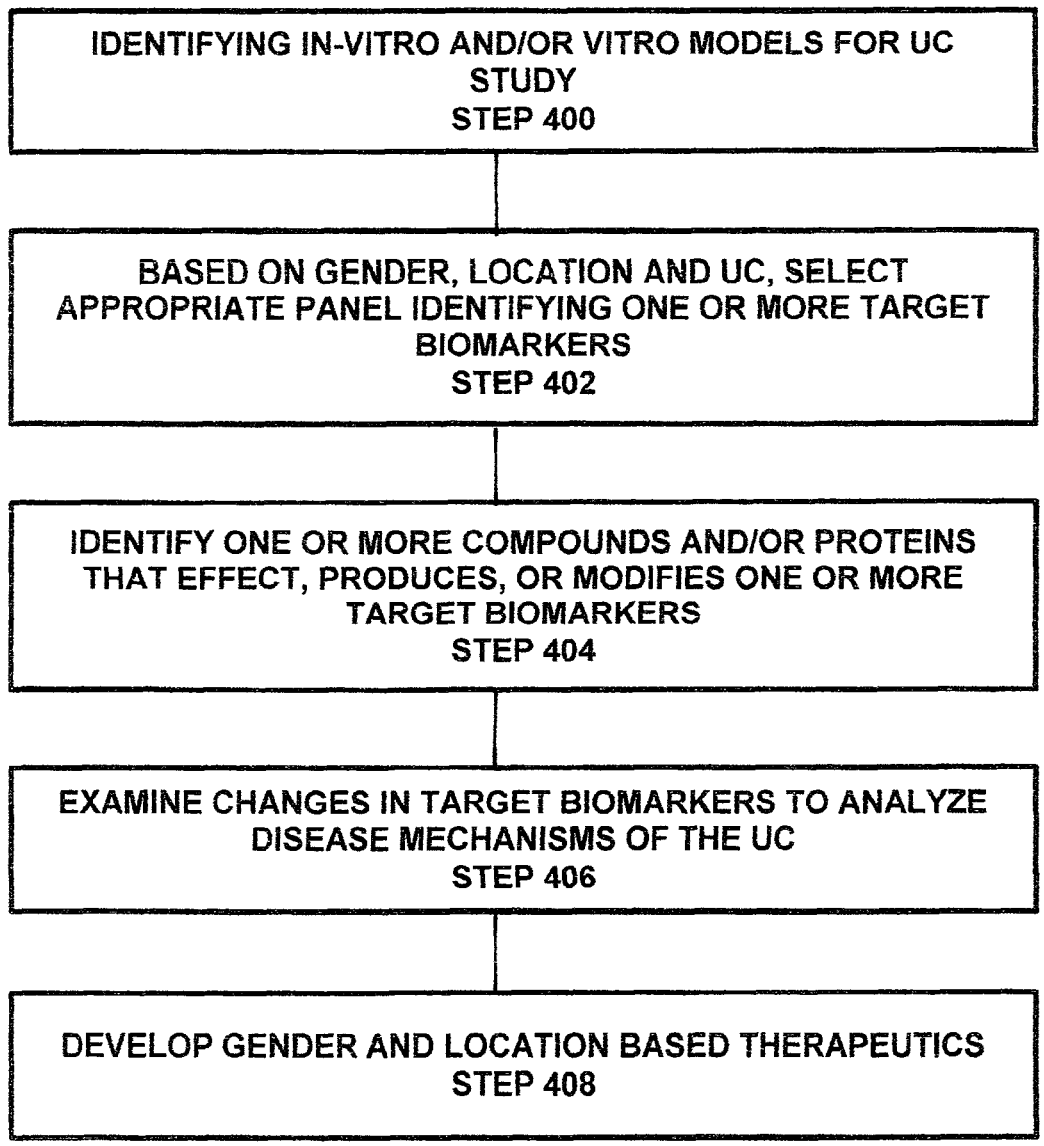
FIG. 18 is a flow diagram of the general methodology of a preferred embodiment of the invention showing the process used for drug development, compound screening, diagnostics and monitoring therapeutic responses using the system of the subject invention.

It should now be understood that the panels of target biomarkers identified for the specific UC conditions and in conjunction with other clinical factors, is used to tailor treatments for individual patients including selecting specific drug treatments and administration regimes, as well used for developing treatments, therapies and medications. In a preferred embodiment, as shown in FIG. 18, the system and process of the subject invention further comprises the steps of identifying in-vitro (cell based) and/or in vivo (animal) models for UC study (step 400). It should be understood that as used herein models can be individual (patient) or animal subjects for use in the study. For a particular gender and UC, the appropriate panel identifying one or more target biomarkers is selected (step 402). One or more compounds and/or proteins that effect, produces, or modifies the one or more target biomarkers are identified (step 404) using standard procedures. Utilizing the changes in the one or more target biomarkers caused by the one or more compounds and/or proteins, disease mechanisms of the UC are analyzed (step 406). It should now be apparent to one skilled in the art that the changes to the identified target biomarkers caused by various compounds and/or proteins permits the creation of new, safe, effective and gender and location-based therapeutics to be developed (step 408). For example, in a non-limiting illustration, medications can be conventionally developed that modifies levels of target biomarkers in a blood component created from a blood sample from a model suffering from UC until such levels fall within a range of prescribed levels of target biomarkers. In another non-limiting illustration, after medication has been administered to the model and given time to react, the levels of the target biomarkers in a blood component created after treatment are compared to levels of the target biomarkers in a blood component created prior to treatment and the effectiveness of the new drug therapy is determined. For example, if the treatment alters one or more of the target biomarkers the efficacy of the administered medication can be determined and if the treatment is not effective, changes can be made to the therapy. If the model shows significant difference in levels of the target biomarkers it can be determined that the proscribed medication is improving the model's condition or is not effective in improving the model's condition. Using the process and system of the subject invention effective dosage of the medication can also be conventionally determined.

Accordingly, the process and system of the subject invention is directed to a more effective, individual (personalized-medicine) based treatment regimen which is built on panels of clinical identified biomarkers. It should now be apparent that the process and system of the subject invention provides an accurate and easy to administer process that can be used for the diagnosis, prognosis, and therapy alternatives for the treatment of UC. In a preferred embodiment of the invention the process of system of the subject invention provides means whereby panels identifying target biomarkers operate as drug targets that are conventionally used to develop new medications and therapies effective for the treatment of UC patients. For example, if a patient shows significant difference in levels of the target biomarkers it can be determined that the proscribed medication is improving or not improving the patient's condition.

In another preferred embodiment of the invention the process and system use panels of target biomarkers as a screening mechanism to conventionally identify therapeutic compounds that may have a therapeutic benefit and potential use for medications to treat UC patients. For example, by examining target biomarkers for a particular UC condition, compounds and/or proteins can be identified that are known to effect, produce, modify, or change one or more of the target biomarkers. Such compounds and/or proteins can then be used to create medications for that particular UC condition.

In another preferred embodiment of the invention, the process and system use panels of target biomarkers such that by comparing changes in the level of one or more of the target markers, as described above, therapeutic effectiveness of medications can be administered to UC patients.

In another preferred embodiment of the invention the process and system of the subject invention operates to identify additional proteins, both upstream and downstream, of the disease pathway for a particular UC condition. Such proteins are then used as additional target biomarkers for creating medications for the particular UC condition. Further, after such proteins are identified changes therein (and their effect on target biomarkers) are determined, such information is used to provide insight into the disease mechanism of the particular UC condition.

In another preferred embodiment of the invention, the process and system of subject invention uses panels of target biomarkers to monitor the therapeutic efficacy of the medication being administered to a UC patient.

Process for Determining the Risk of Disease Development Prior to Diagnosis

The process and system of a preferred embodiment of the invention is directed to a more effective and earlier diagnosis of inflammatory bowel disease which then can be used to make a better prognostic and therapeutic outcome. It has now been found that pre-clinical intestinal inflammation can be represented by changes in non-intestinal specific circulating serum proteins and serum antibodies to immunogens, and autoantigens and their relationship to each other. Six serum proteins and three serum antibodies have been selected: angiotensin converting enzyme (ACE), C-reactive protein (CRP), granulocyte colony stimulating factor (CSF3), haptoglobin (HP), solble intracellular adhesion molecule 1 (sICAM1), Resistin (RETN), perinuclear anti cytoplasmic auto-antibody (pANCA), Scl70 auto-antibody, and anti-tetanus toxoid. Serum markers (predictive target biomarkers) are used for preclinical diagnosis and are associated with antibody titers to bacterial and fungal antigens as well as two non-specific inflammatory proteins. In the process of the subject invention, these predictive target biomarkers which are circulating proteins that are indicative of early changes in antioxidation, tissue and circulation homeostasis, endothelial adhesive changes, granulocyte differentiation and function, cellular energy metabolism, as well as inflammatory processes are used for pre-clinical diagnosis of inflammatory bowel diseases. Total protein in the circulating serum was measured to determine the quantity of a specific protein (specific predictive target biomarker) and the percentage of the total circulating serum protein pool.

In developing the process of determining the risk of inflammatory bowel disease (IBD), including Crohn's disease and ulcerative colitis (referred collectively as "Disease") for an individual prior to the individual diagnosis of the Disease, it was known that non-intestinal specific circulating serum proteins and serum antibodies associated with pre-clinical diagnoses of the Disease existed but had not been identified. Because individuals are often subject to various external environments that are not optimal, such as military personnel that are deployed to various parts of the world, and need to be physically capable of operating and performing critical assignments with little notice. It is therefore desirable to predict an individual's risk of developing a Disease prior to its diagnosis. In developing the subject invention, it was desirable to use the Military Serum Repository that provided samples that would allow environmental change and/or impactful stress status of the individual to be a factor. Accordingly, a study was performed using 300 samples from the Military Serum Repository that incorporated gender as well as environmental change and/or impactful stress status using three populations (control, Crohn's and UC).

Using ICD-9 codes for each Disease, cases that had been identified within three years of sample acquisition were selected and diagnosis was confirmed by at least two visits with the same ICD-9 code. Fifty UC and fifty Crohn's repository serum samples were obtained along with 25-UC matched controls and 25-Crohn's matched controls were obtained. Two such samples were obtained. A pre-sample was taken anytime up to and prior to two years of diagnosis (pre-serum) and a post sample taken within one year of diagnosis (post serum). Controls were age, gender, race and time matched. Six serum proteins were identified (ACE, RETN, CSF3, HP, CRP, sICAM1 and three antibody titers, pANCA, SCL70 and anti-tetanus toxoid (collectively referred to as "predictive target biomarkers") and were tested along with the total serum protein concentration for each of the three-hundred samples. The serum samples were analyzed using Disease, gender and environmental change and/or impactful stress status and univariate and conventional multivariate statistics and algorithm generation were performed. The data were transformed using the logit for the X-specific protein/total serum protein and the LN for the three serum antibodies. The study showed that Disease could be detected prior to diagnosis when either environmental change/impact stress was accounted as well as when it was not.

In a preferred embodiment of the invention, serum samples were obtained and the predictive target biomarkers ACE, RETN, CSF3, HP, CRP, SICAM1 and three antibody titers pANCA, SCL70 and anti-tetanus toxoid were analyzed (actual serum concentrations) and were divided and a ratio of their concentrations to total serum protein concentrations were calculated to determine what percentage of the level of the predictive target biomarker to the level of total protein in obtained serum samples.

Using gene functional and neighborhood enrichment programs, it was found that these nine analytes can be used to determine how an individual's biosystem changes prior to Disease diagnosis and how environmental change and/or impactful stress and the changes in environment effects detectable concentrations of these analytes. Based on the results of the study, four prediction target biomarker panels and four prediction logistic regression models were created based on the 9 analytes and their relationships and are used to determine and make a predictive outcome for an individual that includes the individual's risk for developing a Disease.

Figure 19:
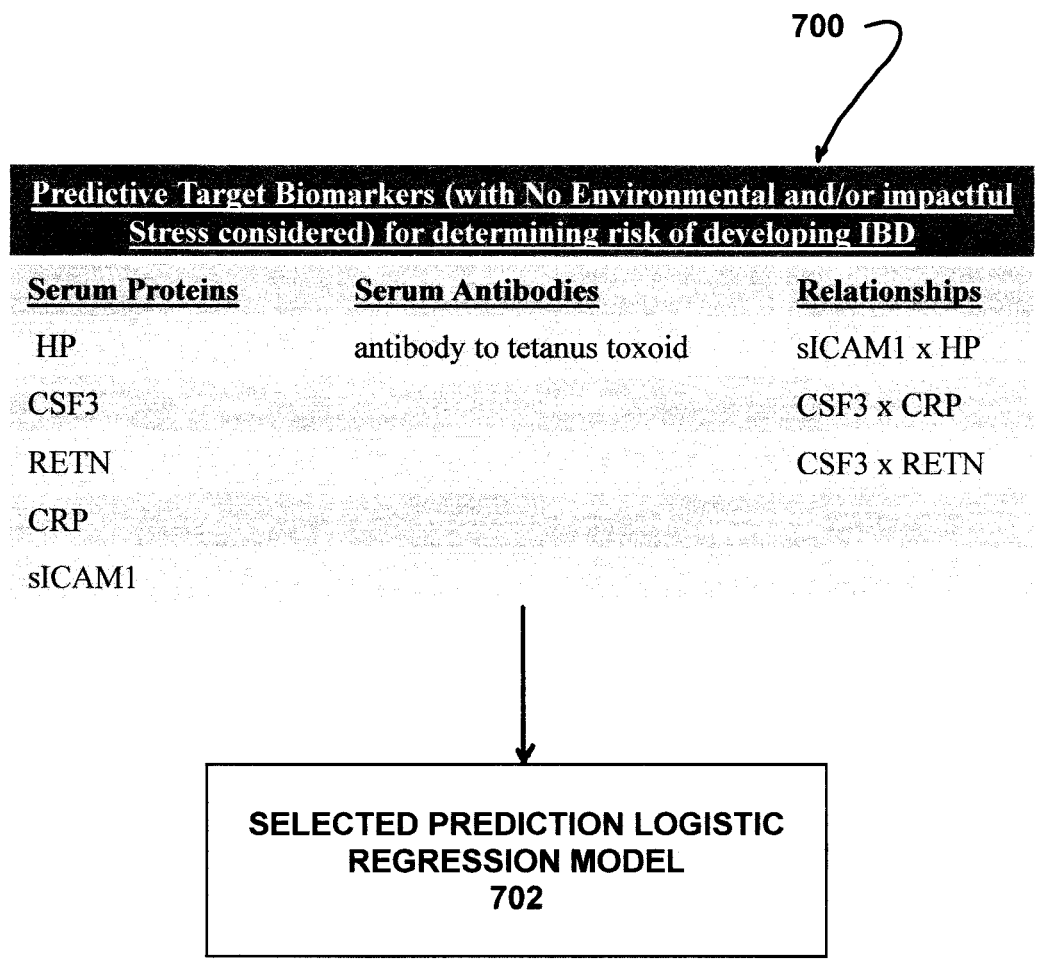
FIG. 19 shows a first prediction panel of predictive target biomarkers for use in determining the risk of an individual developing Inflammatory Bowel Disease (IBD) without Environmental Change and/or Impactful Stress being considered.

The first prediction panel of predictive target biomarkers for use in determining the risk of an individual developing Inflammatory Bowel Disease (IBD) without environmental change and/or impactful stress of the individual being considered 700 is shown in FIG. 19 and the first prediction logistic regression model created and used for determining a risk value for an individual with respect to the individual developing IBD (with environmental change and/or impactful stress not being a consideration) 702 is:

Log $(p/1ip) = -641.8833706 + 71.65755693 \times$ Haptoglobin$-41.87442414 \times$ GCSF$-45.27490174 \times$ RETN$-16.22723673 \times$ CRP$-1.029456032 \times$ Antibody TT$+14.476981343 \times$ sICAM$+5.667294456 \times$ (sICAM$\times$Haptoglobin)$-0.80715758 \times$ (GCSF$\times$CRP)$-2.288843531 \times$ (GCSF$\times$RETN).

Figure 20:
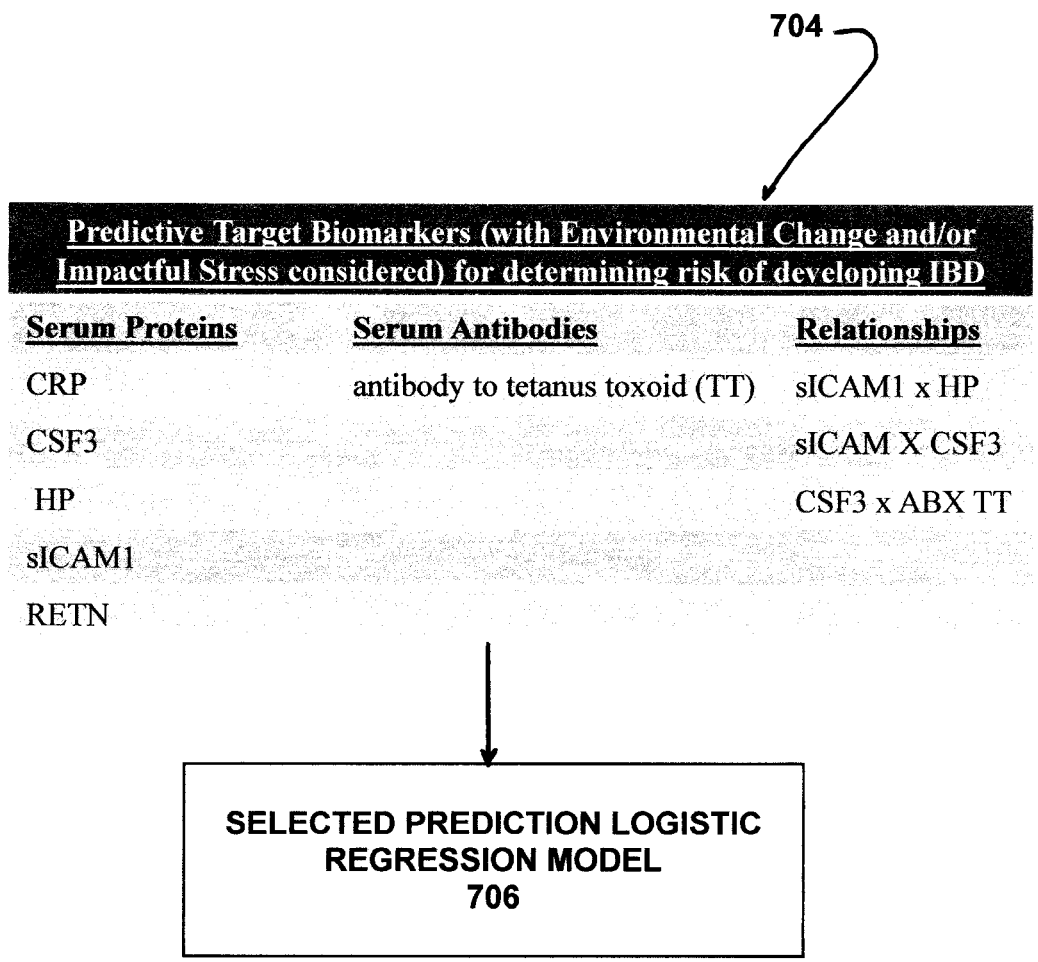
FIG. 20 shows a second prediction panel of predictive target biomarkers for use in determining the risk of an individual developing Inflammatory Bowel Disease (IBD) with Environmental Change and/or Impactful Stress being considered.

The second prediction panel of predictive target biomarkers for use in determining the risk of an individual developing Inflammatory Bowel Disease (IBD) with environmental change and/or impactful stress of the individual being considered 704 is shown in FIG. 20 and the second prediction logistic regression model created and used for determining a risk value for an individual with respect to the individual developing IBD (with Environmental Change and/or Impactful Stress of the individual being considered) 706 is:

Log $(p/1ip) = 1101.571616 - 0.813305575 \times$ Environmental Change and/or Impactful Stress)$-104.1257102 \times$ sICAM$-62.63858365 \times$ GCSF$-5.604142451 \times$ sICAM$\times$GCSF$+65.611507602 \times$ HP$+5.107130532 \times$ sICAM$\times$HP$-36.81637743 \times$ TT$-1.711888269 \times$ GCSF$\times$TT$+0.767135503 \times$ CRP$+1.770741857 \times$ RETN.

(1=Environmental Change and/or Impactful Stress, 0=Status quo)

It should be understood that as used herein "Environmental Change and/or Impactful Stress" includes military deployment and environmental change (such as being assigned to a location outside the individual's native country). Further, it should be understood that Environmental Change and/or Impactful Stress is not limited to individuals that have been relocated but can include individuals that have been subjected to new environmental conditions, are exposed to impactful stress due to a variety of reasons, including, but not limited to stressful family conditions, new lifestyle conditions, new work environments, and other conditions that may result in the individual experiencing high impactful stress lifestyle changes (collectively referred to as "Life Style Factors").

Figure 21:
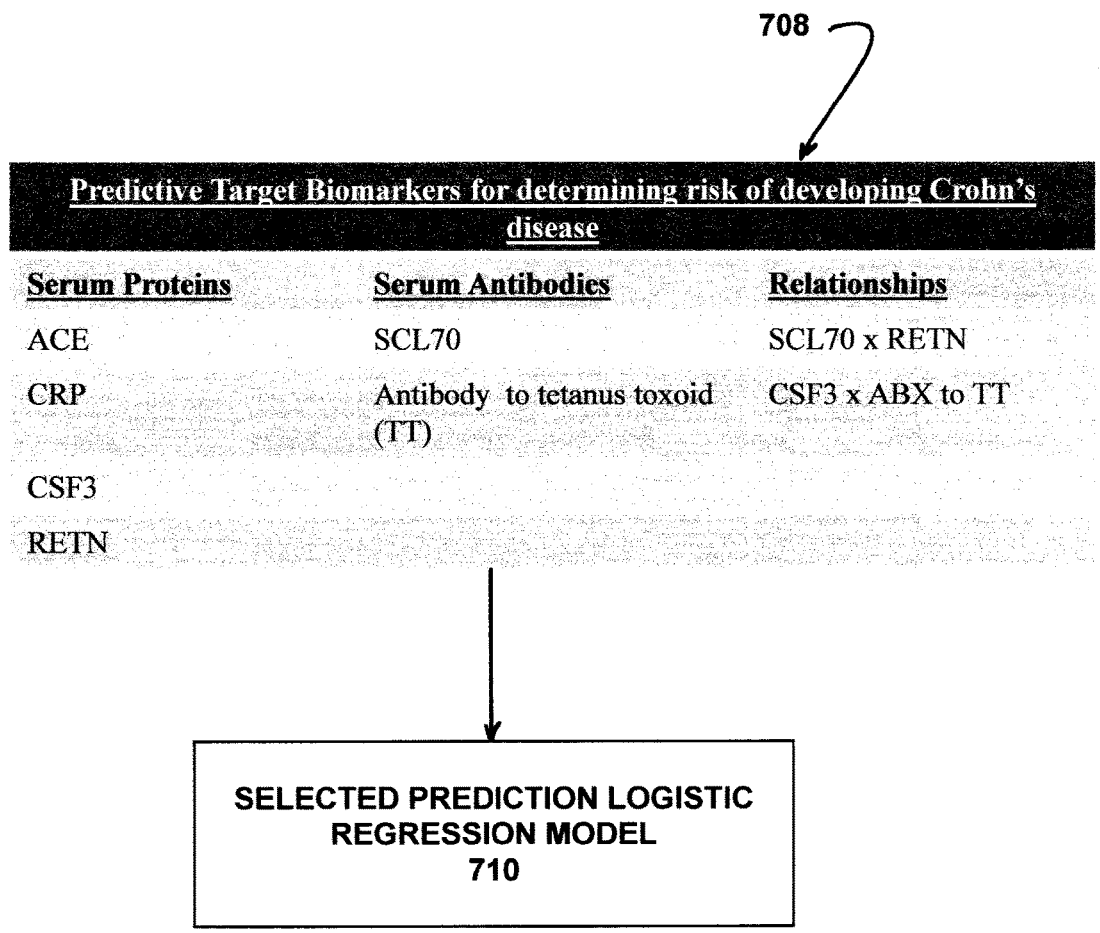
FIG. 21 shows a third prediction panel of predictive target biomarkers for use in determining the risk of an individual developing Crohn's disease.

The third prediction panel of predictive target biomarkers for use in determining the risk of an individual developing Crohn's disease 708 is shown in FIG. 21 and the third prediction logistic regression model created and used to determine a risk value of an individual with respect to developing Crohn's disease 710 is:

Log $(p/1ip) = -174.4 + 171.2 \times$ SLC70$-4.0 \times$ AcE$-32.2 \times$ RETN$+1.1 \times$ CRP$+15.9 \times$ GCSF$-57.4 \times$ TT$+11.6 \times$ (sICAM$\times$RETN)$-2.7 \times$ (GCSF$\times$TT).

Figure 22:
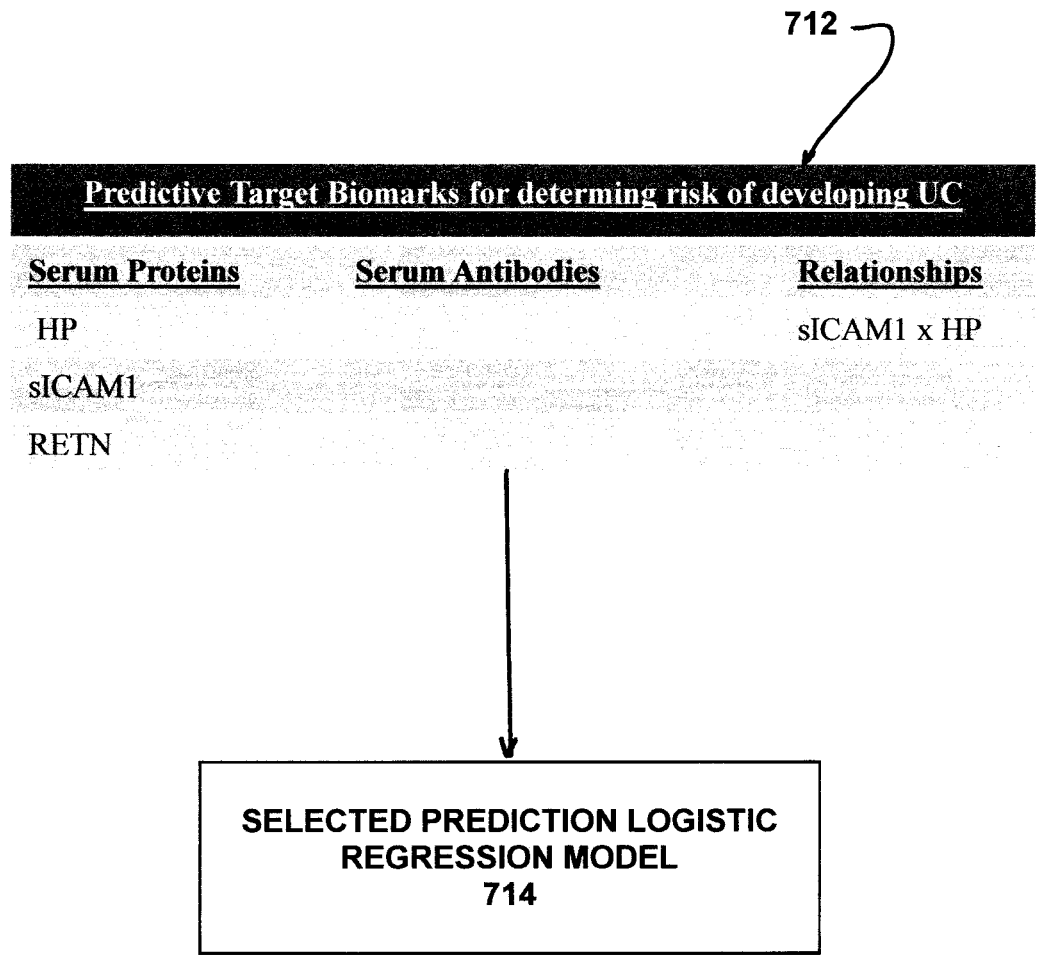
FIG. 22 shows a fourth prediction panel of predictive target biomarkers for use in determining the risk of an individual developing ulcerative colitis.

The fourth prediction panel of predictive target biomarkers for use in determining the risk of an individual developing ulcerative colitis 712 is shown in FIG. 22 and the fourth prediction logistic regression model created and used to determine the risk value of an individual developing ulcerative colitis 714 is:

Log $(p/1-p) = 221.7 + 2.2 \times$ Resistin$+15.1 \times$ sICAM$+61.5 \times$ Haptoglobin$+4.9 \times$ (sICAM$\times$Haptoglobin).

The prediction logistic regression models use serum protein values (logit value of X protein µg/ml/total serum protein concentration µg/ml). Serum antibody values used in the prediction logistic regression models were log transformation value of antibody units.

Based on statistical analysis of the data obtained in study of the samples obtained from the Military Serum Repository and information obtained with regard to the individuals that provided the samples, a cut-off value (a risk value that is above the cut-off value is deemed to indicate that the individual is at an intermediate or at a high risk of developing or having Disease) of predicted probability of an individual developing Disease was determined such that a risk value calculated using a prediction logistic regression model panel is above the cut-off value, the risk that the individual having or developing a Disease is deemed intermediate or at a high risk. It was found that the cut-off value of predicted probability of an individual developing IBD (with deployment of the individual not being a consideration) was determined to be 0.68. The cut-off value of predicted probability of an individual developing IBD (with deployment of the individual being considered) is 0.56. The cut-off value of predicted probability of an individual developing Crohn's disease is 0.5 and the cut-off value of predicted probability of an individual developing ulcerative colitis is 0.52. It should be understood that an individual having a risk value that approaches a cut-off value, such as within 0.1, should be evaluated by a physician. For example, the physician should review the individual's profile that includes family history of Disease, age of the individual, over-all health of the individual and various Life Style Factors experienced or being experienced by the individual (collectively referred to as "Disease Factors"). Such Disease Factors should be taken into consideration by the physician to determine if the individual is or is not at risk for developing Disease and/or if further testing should be conducted and/or Disease treatment by administered.

Figure 23:
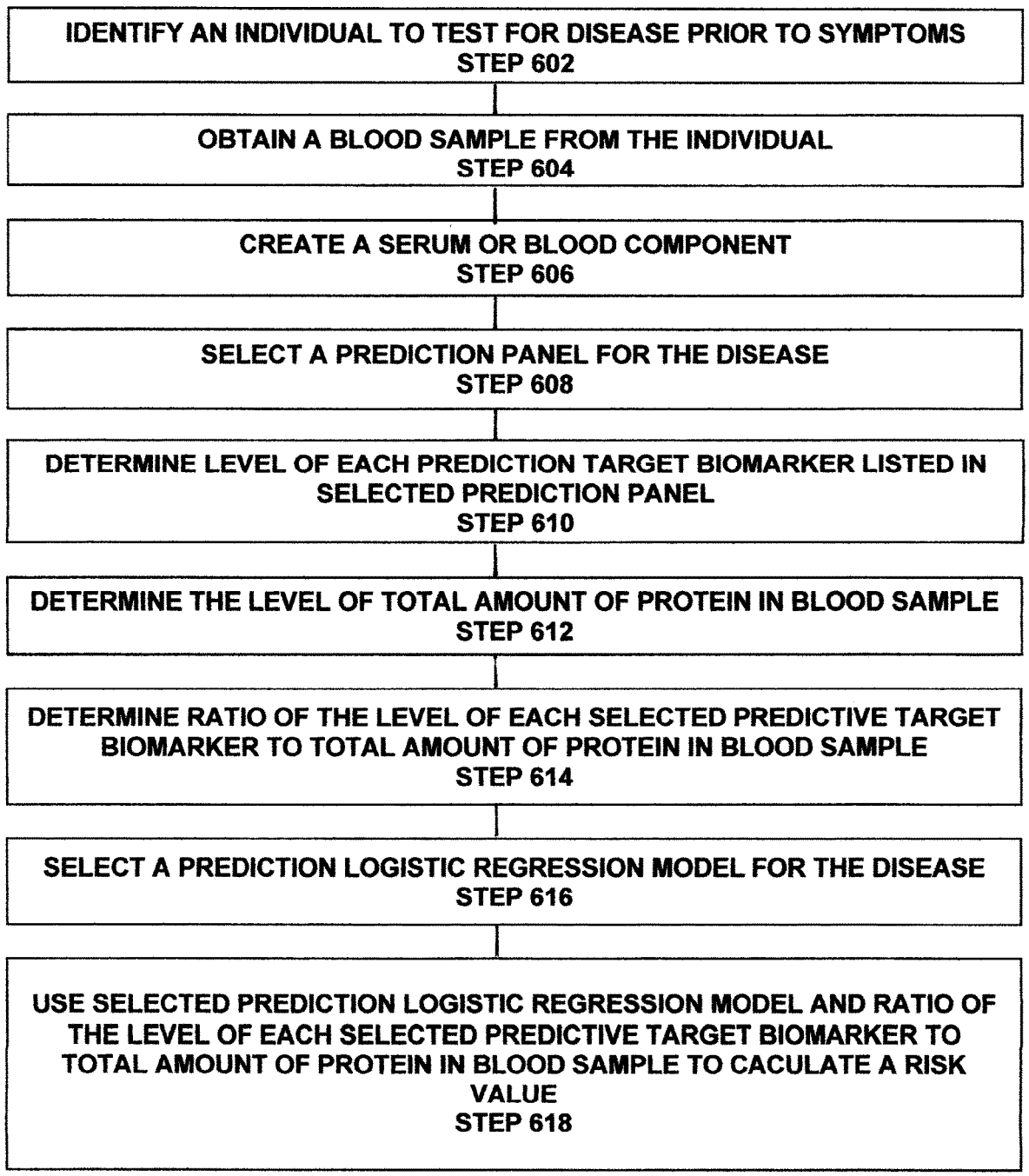
FIG. 23 is a flow diagram of the general methodology of a preferred embodiment of the invention showing the process of identifying individuals having a high risk of developing IBD and a method of treatment.
Figure 24:
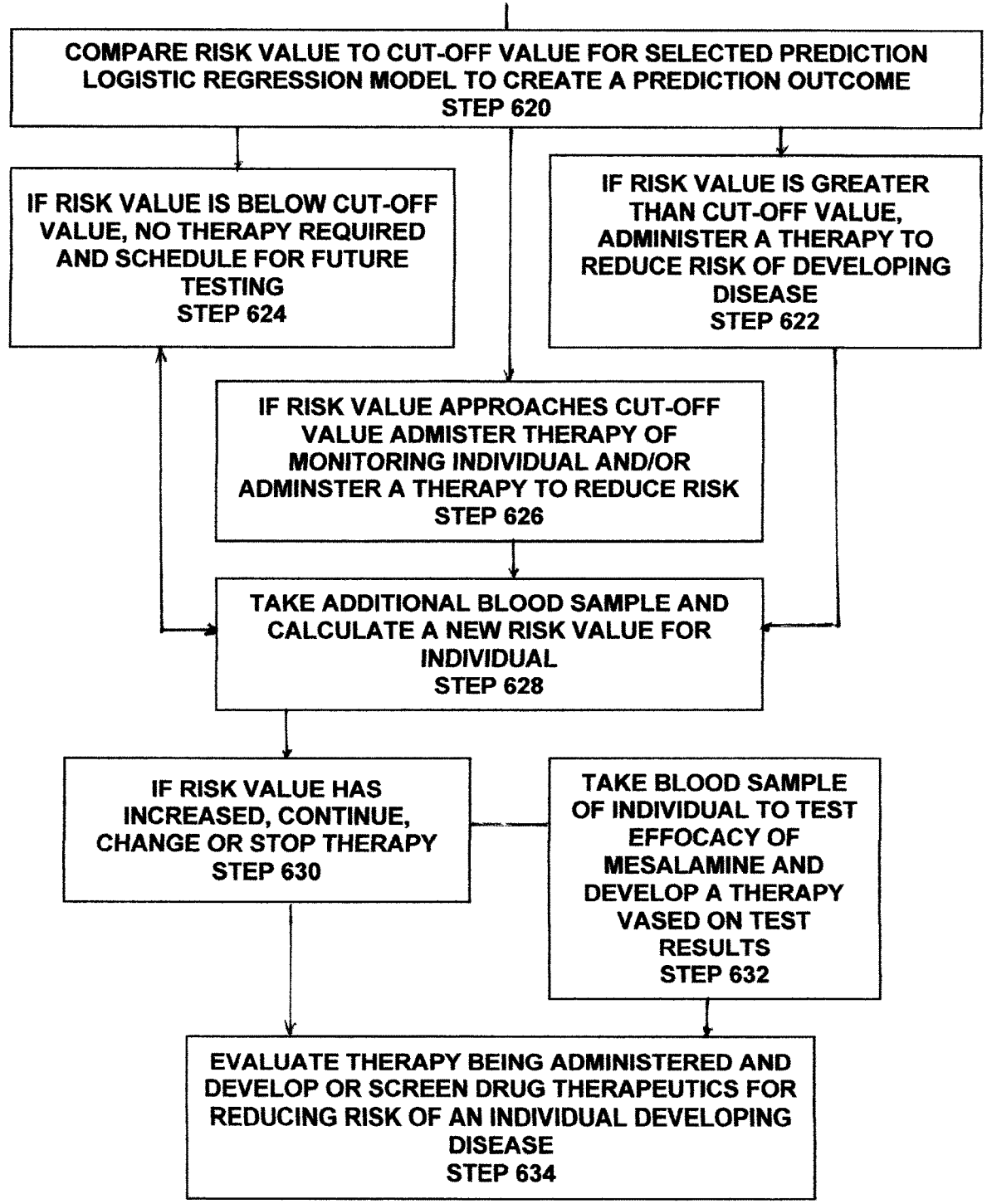
FIG. 24 is a continuation of the flow diagram of FIG. 23.

Referring to FIGS. 23 and 24, the system and process for predicting the risk of an individual developing Disease is illustrated. A preferred embodiment the process of determining the risk of an individual developing Disease comprises the steps of: identifying an individual that should be tested for a Disease prior to showing signs of the Disease (step 602); obtaining a blood sample (preferably, the step of taking a blood sample from an individual is prior to the individual's environmental change and/or impactful stress) from the individual (step 604) and creating a serum or blood component (step 606); selecting a prediction panel for the Disease (step 608); determining the level (amount) of each predictive target biomarkers listed in the prediction panel for the Disease in the blood sample (serum or blood component) (step 610); determining the level (amount) of total amount of protein in the blood sample (serum or blood component) (step 612) and determining a ratio of the level of each selected predictive target biomarker to the total amount of protein in the blood sample (step 614); selecting a prediction logistic regression model for the Disease (step 616) and using the selected prediction logistic regression model to calculate a risk value for the individual developing the Disease (step 618); and comparing the risk value to a cut-off value for the selected prediction logistic regression model (step 620) to create a prediction outcome, such as an indication that the individual is at a low, intermediate or high risk of developing Disease. If the risk value is greater than the cut-off value (the individual is considered at an intermediate or high risk), the process includes the step of administering a therapy to reduce the risk of developing Disease (step 622). If the risk value is below the cut-off value (the individual is considered at a low risk) and the individual requires no therapy or monitoring. It should be understood that depending on the medical history of the individual as well as Disease Factors, additional testing dates for the individual may be scheduled (step 624). If the risk value approaches the cut-off value, such as within 0.1 of the cut-off value, the individual is considered at an intermediate risk and the process includes the step of administering a therapy to monitor the individual for an increase in the risk of developing Disease or for signs (symptoms) of Disease (step 626).

It should be understood that the step of administering a therapy to reduce the risk of developing Disease can include administering a treatment (such as a medication or lifestyle change, changing the individual's diet or administering a treatment to change various Lifestyle Factors) to the individual. In a preferred embodiment, if an individual is at an intermediate or high risk of developing Disease, the process includes taking additional blood sample(s) (step 628). Using the levels (amounts) of the predictive target biomarkers in the second blood sample and the level (amount) of total protein in the second blood component the selected prediction logistic regression model is used to calculate a new risk value for the individual to determine if the risk value for the individual has increased, decreased or remained the change (step 630). Based on the new risk value, the treatment(s) being administered to the individual can be evaluated and the treatment(s) can be continued, changed or stopped. In another preferred embodiment of the invention, if an individual having a risk of Disease begins to show symptom of the Disease, the process includes predicting the efficacy of mesalamine for the treatment of the Disease as described above (step 632).

In a preferred embodiment of the invention, the process further includes the steps evaluating the treatment being administered to the individual to develop or screen drug therapeutics for reducing the risk of an individual developing Disease or for slowing down the progression of the Disease (step 634).

It should be understood that changes in the levels of the predictive target biomarkers or changes in the risk probability value can be used to determine the efficacy of an administered medication or treatment. For example, if the patient shows significant difference in levels of the predictive target biomarkers or the calculated risk probability value for the individual, it can be determined that the proscribed medication or treatment is reducing the risk of developing Disease. It should now be apparent to one skilled in the art that the subject invention allows for the development of new personalized IBS drugs for the prevention of Disease.

It should now be apparent to one skilled in the art that the present invention provides a process and system whereby panels of predictive target biomarkers are used for risk assessment and can be used to develop treatments for individuals expressing higher risk of developing Disease and thus provides substantive value in various aspects of patient care management. It should also now be apparent to one skilled in the art that the process and system of the subject invention prevents or reduces the likelihood of treatment using ineffective medications as well as reducing the possibility of delay in treatment of the Disease. Accordingly, the use of the process and system of the subject invention is very beneficial to individuals, the prescribing practitioner, and insurance companies.

It should now be understood that the panels of predictive target biomarkers and the prediction logistic regression models can be used to tailor treatments for individuals including selecting specific drug treatments and administration regimes, as well used for developing treatments, therapies and medications and permits the creation of new, safe, effective therapeutics to be developed. For example, in a non-limiting illustration medications and therapies can be conventionally developed using the system and process of the subject invention that modifies levels of predictive target biomarkers or changes the probability values until such levels fall outside the moderate or high-risk probability that the individual will develop a Disease. In another non-limiting illustration, after medication or treatment has been administered to a moderate or high-risk individual, the process and system can be used to determine the effectiveness of the medication or treatment. Using the process and system of the subject invention effective dosage of a medication can also be conventionally determined.

Although the foregoing invention has been described in some detail for purposes of clarity of understandings, it will be apparent that certain changes and modifications may be practiced within the scope of the appended claims. It should now be apparent that the various embodiments presented can be easily modified while keeping within the scope and spirit of the subject invention. Accordingly, it should be understood that the present disclosure is to be considered as exemplary of the principals of the invention and is not intended to limit the invention to the embodiments and the specific examples illustrated and the invention is not to be limited to the details given herein, but may be modified within the scope and equivalents of the descriptions and examples contained herein.

The invention claimed is:

1. A process of predicting an individual's risk of developing inflammatory bowel disease (IBD) and treating the individual that has a risk of developing IBD, the process comprises the steps of:

selecting an individual to be tested prior to the individual showing symptoms of IBD such that the individual would be diagnose with having IBD;

obtaining a first blood sample of the selected individual;

examining the blood sample to obtain a level of each predictive target biomarker listed in a prediction panel of predictive target biomarkers;

determining the total level of protein in the blood sample;

using a prediction logistic regression model that uses the predictive target biomarkers listed in the prediction panel of predictive target biomarkers for predicting the risk of an individual developing IBD and using the logistic regression model and the levels of each predictive target biomarker and the total level of protein in the blood sample to calculate a risk value for the selected individual developing IBD; and determining if the risk value for the selected individual developing IBD is above or below a cut-off value for the prediction logistic regression model;

wherein the prediction panel of predictive target biomarkers for use in predicting the risk of an individual developing IBD comprises the predictive target biomarkers of Haptoglobin (HP), Granulocyte Colony Stimulating Factor (GCSF), Resistin (RETN), C-Reactive Protein (CRP), Soluble Interacellular Adhesion Molecule 1 (sICAM1) and Antibody TT and identifies the relationships of sICAM1×HP, GCSF×CRP and GCSF×RETN;

wherein the prediction logistic regression model for determining the risk value for an individual developing IBD is: Log (p/1ip)=−641.8833706+71.65755693×HP−41.87442414×GCSF−45.27490174×RETN−16.22723673×CRP−1.029456032×Antibody TT+14.476981343×sICAM1+5.667294456×(sICAM1×HP)−0.80715758×(GCSF×CRP)−2.288843531×(GCSF×RETN), wherein the cut-off value of is 0.68;

wherein if the determined risk value for the selected individual developing IBD is greater than the cut-off value for the prediction logistic regression model, the process includes administering a therapy to the selected individual to reduce the risk of the selected individual developing IBD, wherein said therapy includes administering a medication for treating IBD, repeating the process of determining the risk value for the selected individual developing IBD, wherein if the risk value increases or remains the same, making modifications to the therapy being administered to the selected individual and repeating the process of determining the risk value for the selected individual developing IBD; and continue the therapy or continue to modify the therapy until the risk value for the selected individual developing IBD is below the cut-off value for the prediction logistic regression model; and wherein if the risk value for the selected individual developing IBD is below the cut-off value for the prediction logistic regression model used for determining the risk value of an individual developing IBD, the process includes using Disease Factors of the selected individual to determine if the process is to be performed again at a future date or administer a therapy to the selected individual when the selected individual is diagnosed with IBD, Crohn's disease or UC for treating IBD, Crohn's disease or UC.

2. The process of claim 1, wherein if the risk value of the selected individual developing IBD is greater than the cut-off value for the prediction logistic regression model used for determining the risk value of an individual developing IBD and/or if the therapy and any modifications in the therapy being administered to the selected individual for reducing the risk value for developing IBD does not reduce the risk value of the selected individual below the cut-off value of the reduction logistic regression model used for determining the risk value of an individual developing IBD, the process includes the steps of:

obtaining a blood sample of the selected individual;

examining the blood sample to obtain a level of each predictive target biomarker listed in a prediction panel of predictive target biomarkers for predicting the risk of an individual developing Crohn's disease and a total level of protein in the blood sample;

using a prediction logistic regression model that uses the predictive target biomarkers listed in the prediction panel of predictive target biomarkers to calculate a risk value of the selected individual developing Crohn's disease;

wherein if the calculated risk value for the selected individual of developing Crohn's disease is greater than a cut-off value for the prediction logistic regression model for predicting the risk of an individual developing Crohn's disease, administering a therapy for treating Crohn's disease;

wherein the therapy for treating Crohn's disease includes administering a medication known for treating Crohn's disease and repeating the process of determining the risk value of the selected individual for developing Crohn's disease, wherein if the risk value increases or remains the same, making modifications to the therapy and repeating the process of determining the risk value for developing Crohn's disease and continue with the therapy or modifying the therapy until the risk value of the selected individual for developing Crohn's disease is below a cut-off value for the prediction logistic regression model;

wherein the list of predictive target biomarkers in the predictive prediction panel of predictive target biomarkers for use in determining the risk of an individual developing Crohn's disease comprises the target biomarkers AutoAb to topisomerase type 1 (SLC70), Angiotensin 1 converting enzyme (AcE), RETN, CRP, GCSF and Antibody TT and identifies the relationships of sICAM1×RETN, GCSF×Antibody TT; and wherein the prediction logistic regression model for determining the risk value for an individual developing Crohn's disease is Log (p/1ip)=−174.4+171.2×SLC70−4.0×AcE−32.2×RETN+1.1×CRP+15.9×GCSF−57.4×Antibody TT+11.6×(sICAM1×RETN)−2.7×(GCSF×Antibody TT) and the cut-off value is 0.5.

3. The process of claim 1, wherein if the risk value for the selected individual developing IBD is greater than the cut-off value for the prediction logistic regression model used for determining the risk value of an individual developing IBD and if the therapy and any modifications in the therapy for reducing the risk of the selected individual developing IBD does not reduce the risk value for developing IBD below the cut-off value of the prediction logistic regression model used for determining the risk value of an individual developing IBD, the process includes the steps of:
  obtaining a blood sample of the individual;
  examining the blood sample to obtain a total level of protein in the blood sample and a level of each predictive target biomarker listed in a prediction panel of predictive target biomarkers for determining the risk value of an individual developing UC;
  using a prediction logistic regression model that uses the levels of each predictive target biomarker listed in the prediction panel of predictive target biomarkers and the total level of protein in the blood sample to calculate a risk value for the selected individual developing UC;
  wherein if the risk value for the selected individual developing UC is above a cut-off value for the prediction logistic regression model for use in determining the risk value of an individual developing UC, administering a therapy to the selected individual for treating UC;
  wherein the therapy includes administering a medication for treating UC and repeating the process of determining the risk value for the selected individual developing UC, wherein if the risk value increases or remains the same, making modifications to the therapy for treating UC and repeating the process of determining the risk value for developing UC and continue the therapy or modifying the therapy until the risk value for the selected individual developing UC is below the cut-off value for the prediction logistic regression model for determining the risk value for an individual developing UC;
  wherein the prediction panel of predictive target biomarkers for use in determining the risk of an individual developing UC comprises the target biomarkers of HP, SICAM1 and RETN; and
  wherein the prediction logistic regression model for determining the risk value for an individual developing UC is $\text{Log}(p/1-p) = 221.7 + 2.2 \times \text{RETN} + 15.1 \times \text{sICAM1} + 61.5 \times \text{HP} + 4.9 \times (\text{sICAM1} \times \text{HP})$ and wherein the cut-off value is 0.52.

4. The process of claim 1, wherein if the risk value for the selected individual developing IBD is below the cut-off value for the prediction logistic regression model, the process includes using a second prediction panel of predictive target biomarkers comprising the predictive target biomarkers of sICAM1, GCSF, HP, CRP, RETN and Antibody TT and using a second prediction logistic regression model and the levels of each of the predictive target biomarkers in the second prediction panel of predictive biomarkers and the total level of protein in the blood sample to determine a second risk value, wherein the second prediction logistic regression model is: $\text{Log}(p/1ip) = 1101.571616 - 0.813305575 \times \text{deployment} - 104.1257102 \times \text{sICAM1} - 62.63858365 \times \text{GCSF} - 5.604142451 \times \text{sICAM1} \times \text{GCSF} + 65.611507602 \times \text{HP} + 5.107130532 \times \text{sICAM1} \times \text{HP} - + 1.770741857 \times \text{RETN}$ and wherein the cut-off value is 0.56; and
  wherein if the determined second risk value for the selected individual developing IBD is greater than the cut-off value for the second prediction logistic regression model, the process includes administering a therapy to the selected individual to reduce the risk of the selected individual developing IBD, wherein said therapy includes administering a medication for treating IBD, repeating the process of determining the second risk value for the selected individual developing IBD, wherein if the second risk value increases or remains the same, making modifications to the therapy being administered to the selected individual and repeating the process until the second risk value is below the cut-off value for the second prediction logistic regression model; and
  wherein if the second risk value for the selected individual developing IBD is below the cut-off value for the second prediction logistic regression model used for determining the risk value of an individual developing IBD, the process includes using Disease Factors of the selected individual to determine if the process is to be performed again at a future date or administer a therapy to the selected individual when the selected individual is diagnosed with IBD, Crohn's disease or UC for treating IBD, Crohn's disease or UC.

5. A process of predicting and individual's risk of developing inflammatory bowel disease (IBD), the process comprises the steps of:
  selecting an individual to be tested prior to the individual showing symptoms of IBD such that the individual is diagnosed with having IBD, wherein the individual is further selected based on Disease Factors of the selected individual;
  obtaining a first blood sample of the selected individual;
  examining the blood sample to obtain a level of each predictive target biomarker listed in a prediction panel of predictive target biomarkers for IBD;
  determining the total level of protein in the blood sample;
  using a prediction logistic regression model that uses the predictive target biomarkers listed in the prediction panel of predictive target biomarkers for determining a risk value of an individual developing IBD and using the prediction logistic regression model for predicting the risk of an individual developing IBD and the levels of each predictive target biomarker listed in the prediction panel of predictive target biomarkers for IBD and the total level of protein in the blood sample to calculate a risk value for the selected individual developing IBD;
  determining if the risk value for the selected individual developing IBD is above or below a cut-off value for the prediction logistic regression model for predicting the risk of an individual developing IBD;
  wherein the prediction panel of predictive target biomarkers for use in determining the risk value of an individual developing IBD comprises the predictive target biomarkers of Haptoglobin (HP), Granulocyte Colony Stimulating Factor (GCSF), Resistin (RETN), C-Reactive Protein (CRP), Soluble Interacellular Adhesion Molecule 1 (sICAM1) and Antibody TT and identifies the relationships of sICAM1×HP, GCSF×CRP and GCSF×RETN;
  wherein the prediction logistic regression model for determining the risk value for an individual developing IBD is: $\text{Log}(P/1ip) = -641.8833706 + 71.65755693 \times \text{HP} - 41.87442414 \times \text{GCSF} - 45.27490174 \times \text{RETN} - 16.22723673 \times \text{CRP} - 1.029456032 \times \text{Antibody TT} + 14.476981343 \times \text{sICAM1} + 5.667294456 \times (\text{sICAM1} \times \text{HP}) - 0.80715758 \times (\text{GCSF} \times \text{CRP}) - 2.288843531 \times (\text{GCSF} \times \text{RETN})$, wherein the cut-off value is 0.68;
  using a second prediction panel of predictive target biomarkers and a second prediction logistic regression model for determining the risk of an individual developing IBD, wherein the predictive target biomarkers listed in the second prediction panel of predictive target biomarkers are sICAM1, GCSF, HP, CRP, RETN and Antibody TT and the second prediction logistic regression model is: Log (p/1ip)=1101.571616−0.813305575×deployment−104.1257102×sICAM1−62.63858365×GCSF−5.604142451×sICAM1×GCSF+65.611507602×HP+5.107130532×sICAM1×HP−36.81637743×Antibody TT−1.711888269×GCSF×Antibody TT+0.767135503×CRP+1.770741857×RETN having a cut-off value of 0.56;

wherein if the risk value determined using the first prediction logistic regression model or the risk value determined using the second prediction logistic regression model is greater than the cut-off values for the first prediction logistic regression model or the second prediction logistic regression model, respectively, the process includes using a prediction panel of predictive target biomarkers for use in determining the risk of an individual developing Crohn's disease having a list of predictive target biomarkers for use in determining the risk value of an individual developing Crohn's disease;

examining the blood sample to obtain a total level of protein in the blood sample and a level of each predictive target biomarker listed in the prediction panel of predictive target biomarkers for use in determining a risk value of an individual developing Crohn's disease;

using a prediction logistic regression model for determining the risk of an individual developing Crohn's disease that uses the total level of protein in the blood sample and the level of each predictive target biomarker listed in the prediction panel of target biomarkers for determining the risk of an individual developing Crohn's disease to determine a risk value of the selected individual developing Crohn's disease;

determining if the risk value for the selected individual developing Crohn's disease is above or below a cut-off value for the prediction logistic regression model for use in determining the risk of an individual developing Crohn's disease;

wherein the prediction panel of predictive target biomarkers for use in determining the risk of an individual developing Crohn's disease comprises AutoAb to topisomerase type 1 (SLC70), Angiotensin 1 converting enzyme (AcE), RETN, CRP, GCSF and Antibody TT and identifies the relationships of sICAM1×RETN, GCSF×Antibody TT;

wherein the prediction logistic regression model for determining the risk value for an individual developing Crohn's disease is Log (p/1ip)=−174.4+171.2×SLC70−4.0×AcE−32.2×RETN+1.1×CRP+15.9×GCSF−57.4×Antibody TT+11.6×(sICAM1×RETN)−2.7×(GCSF×Antibody TT and wherein the cut-off value is 0.5;

wherein if the risk value for the selected individual developing Crohn's disease is below the cut-off value for the prediction logistic regression model for use in determining the risk of an individual developing Crohn's disease, the process includes the steps of using a prediction panel of predictive target biomarkers for use in determining the risk of an individual developing ulcerative colitis (UC) to determine a risk value of the selected individual developing UC, wherein the prediction panel of predictive target biomarkers for use in determining the risk of an individual developing UC comprises the predictive target biomarkers of HP, SICAM1 and RETN, and identifies the relationship of sICAM1×HP;

examining the blood sample to obtain a total level of protein in the blood sample and a level of each predictive target biomarker listed in the prediction panel of predictive target biomarkers for use in determining the risk of the individual developing UC;

using a prediction logistic regression model for use in determining a risk value of an individual developing UC and using the logistic regression model and the total level of protein in the blood sample and the levels of each predictive target biomarker listed in the prediction panel of predictive target biomarkers for use in determining the risk value of an individual developing UC to calculate a risk value for selected individual developing UC;

determining if the risk value for the selected individual developing UC is above or below a cut-off value for the prediction logistic regression model for use in determining the risk of an individual developing UC;

wherein the prediction logistic regression model for determining the risk value for an individual developing UC is Log (p/1−p)=221.7+2.2×RETN+15.1×sICAM1+61.5×HP+4.9×(sICAM1×HP) and the cut-off value is 0.52;

wherein if the risk value for the selected individual developing IBD or Crohn's disease or UC is greater than the cut-off value for the prediction logistic regression model for determining the risk of an individual developing IBD, Crohn's disease or UC, respectively, the process includes the step of administering a therapy known to treat IBD or Crohn's disease or UC and repeating the process to determine if the risk value of developing IBD or Crohn's disease or UC is decreasing, remaining the same or increasing and if the risk value is remaining the same or increasing, modifying the therapy until the risk value of developing IBD or Crohn's disease or UC is below the cut-off value for developing IBD, Crohn's disease or UC, respectively; and wherein if the risk values for the selected individual developing IBD and Crohn's disease and UC are below the cut-off values for the prediction logistic regression model used for determining the risk value of an individual developing IBD, Crohn's disease and UC, respectively, the process includes using Disease Factors of the selected individual to determine if the process is to be performed again at a future date or administer a therapy to the selected individual when the selected individual is diagnosed with IBD, Crohn's disease or UC for treating IBD, Crohn's disease or UC.

6. A process of identifying and treating an individual that may have or have a high risk of developing inflammatory bowel disease (IBD) prior to the individual showing symptoms of IBD, the process comprises the steps of:

selecting an individual to be tested, wherein the individual is selected based on the individual not showing symptoms of IBD such that the individual would be diagnosed with having IBD, and Disease Factors of the individual;

obtaining a first blood sample of the selected individual;

using a first prediction panel of predictive target biomarkers for use in predicting the risk of an individual developing IBD, wherein the prediction panel of predictive target biomarkers comprises the predictive target biomarkers of Haptoglobin (HP), Granulocyte Colony Stimulating Factor (GCSF), Resistin (RETN), C-Reactive Protein (CRP), Soluble Intercellular Adhesion Molecule 1 (sICAM1) and Antibody TT and identifies the relationships of sICAM1×HP, GCSF×CRP and GCSF×RETN;

examining the blood sample to obtain a level of each predictive target biomarker listed on the panel of in the prediction panel of predictive target biomarkers;

determining the total level of protein in the blood sample;

using a first prediction logistic regression model for predicting the risk of an individual developing IBD and using the first prediction logistic regression model and the levels of each predictive target biomarker in the first prediction panel of predictive target biomarkers and the total level of protein in the blood sample to calculate a first risk value and determine if the first risk value is above or below the cut-off value for the first prediction logistic regression model;

wherein the first prediction logistic regression model for calculating the risk value of an individual developing IBD is: Log (p/1ip)=−641.8833706+71.65755693×HP−41.87442414×GCSF−45.27490174×RETN−16.22723673×CRP−1.029456032×Antibody TT+14.476981343×sICAM1+5.667294456×(sICAM1×HP)−0.80715758×(GCSF×CRP)−2.288843531×(GCSF×RETN) and wherein the cut-off value is 0.68;

using a second prediction panel of predictive target biomarkers for use in predicting the risk of an individual developing IBD, wherein the second prediction panel of predictive target biomarkers comprises the predictive target biomarkers of sICAM1, GCSF, HP, CRP, RETN and Antibody TT;

using a second prediction logistic regression model for predicting the risk value of an individual developing IBD and the levels of each predictive target biomarker in said second prediction panel of predictive target biomarkers and the total level of protein in the blood sample to calculate a second risk value and determine if the second risk value is above or below the cut-off value for the second prediction logistic regression model, wherein the second prediction logistic regression model is: Log (p/1ip)=1101.571616−0.813305575×deployment−104.1257102×sICAM1−62.63858365×GCSF−5.604142451×sICAM1×GCSF+65.611507602×HP+5.107130532×sICAM1×HP−36.81637743×Antibody TT−1.711888269×GCSF×Antibody TT+0.767135503×CRP+1.770741857×RETN, wherein the cut-off value is 0.56;

wherein if the first risk value for developing IBD is greater than the cut-off value for the first prediction logistic regression model or if the second risk value for developing IBD is greater than the cut-off value for the second prediction logistic regression model, using a prediction logistic regression model, the total level of protein in the blood sample and the level of each predictive target biomarker listed in a prediction panel of predictive target biomarkers for determining the risk of an individual developing Crohn's disease to determine a risk value for the selected individual developing Crohn's disease, wherein the predictive panel of target biomarkers comprises the predictive target biomarkers AutoAb to topisomerase type 1 (SLC70), Angiotensin 1 converting enzyme (AcE), RETN, CRP, GCSF and Antibody TT and identifies the relationships of sICAM1×RETN, GCSF×Antibody TT;

wherein the prediction logistic regression model for determining the risk value for developing Crohn's disease is Log (p/1ip)=−174.4+171.2×SLC70−4.0×AcE−32.2×RETN+1.1×CRP+15.9×GCSF−57.4×Antibody TT+11.6×(sICAM1×RETN)−2.7×(GCSF×Antibody TT), and wherein the cut-off value is 0.5;

wherein if the risk value for developing Crohn's disease is greater than a cut-off value for the prediction logistic regression model for use in determining the risk of an individual developing Crohn's disease, administering a therapy to the selected individual for treating Crohn's disease;

wherein the therapy includes administering a medication for treating Crohn's disease and repeating the process of determining the risk value of the selected individual for developing Crohn's disease and wherein if the risk value remains the same or increases, making modifications to the therapy and repeating the process of determining the risk value for the selected individual developing Crohn's disease and continue with the therapy or modify the therapy until the risk value for the selected individual developing Crohn's disease is below the cut-off value; and wherein the process includes using a prediction panel of predictive target biomarkers for use in determining the risk of an individual developing ulcerative colitis (UC), wherein the prediction panel of predictive target biomarkers for use in determining the risk of an individual developing UC comprises the predictive target biomarkers of HP, SICAM1 and RETN;

examining the blood sample to obtain a level of each predictive target biomarker in the prediction panel of predictive target biomarkers for use in determining the risk of an individual developing UC;

using a prediction logistic regression model for use in determining the risk of an individual developing UC and using the logistic regression model, the total level of protein in the blood sample and the level of each predictive target biomarker listed in the prediction panel of predictive target biomarkers for use in determining the risk of an individual developing UC to calculate a risk value for the selected individual developing UC, wherein the prediction logistic regression model for determining the risk value of an individual developing UC is Log (p/1−p)=221.7+2.2×RETN+15.1×sICAM1+61.5×HP+4.9×(sICAM1×HP), and the cut-off value is 0.52;

determining if the risk value for the selected individual developing UC is above or below a cut-off value for the prediction logistic regression model for use in determining the risk of an individual developing UC;

wherein if the risk value for the selected individual developing UC is greater than the cut-off value for the prediction logistic regression model for use in determining the risk of an individual developing UC, the process includes the step of administering a therapy for treating UC, wherein the therapy includes administering a medication for treating UC and repeating the process of determining the risk value of the selected individual developing UC, wherein if the risk value remains the same or increases, making modifications to the therapy and repeating the process of determining the risk value of the selected individual developing UC and continue with the therapy or modify the therapy until the risk value for the selected individual developing UC is below the cut off value;

wherein if the first risk value for the selected individual developing IBD is greater than the cut-off value for the first prediction logistic regression model or if the second risk value for the selected individual developing IBD is greater than the cut-off value for the second prediction logistic regression model and the risk value for the selected individual developing Crohn's disease is less than the cut-off value for the prediction logistic regression model for developing Crohn's disease and the risk value for the selected individual developing UC is less than the cut-off value for the prediction logistic regression model for developing UC, the process includes administering a therapy to reduce the risk value of the selected individual developing IBD, wherein the therapy includes administering a medication known to treat IBD; and wherein if the risk value for the selected individual developing IBD is below the cut-off value for the prediction logistic regression model used for determining the risk value of an individual developing IBD, the process includes using Disease Factors of the selected individual to determine if the process is to be performed again at a future date or administer a therapy to the selected individual when the selected individual is diagnosed with IBD, Crohn's disease or UC for treating IBD, Crohn's disease or UC.

* * * * *